(12) United States Patent
Shahriari et al.

(10) Patent No.: US 10,624,770 B2
(45) Date of Patent: *Apr. 21, 2020

(54) HYBRID DEVICE FOR SURGICAL AORTIC REPAIR CONFIGURED FOR ADAPTABILITY OF ORGANS OF VARIOUS ANATOMICAL CHARACTERISTICS AND METHOD OF USING THE SAME

(71) Applicant: Ascyrus Medical, LLC, Boca Raton, FL (US)

(72) Inventors: Ali Shahriari, Boca Raton, FL (US); Eric Leopold, Boca Raton, FL (US)

(73) Assignee: Ascyrus Medical, LLC, Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/507,168

(22) Filed: Jul. 10, 2019

(65) Prior Publication Data

US 2019/0328558 A1    Oct. 31, 2019

Related U.S. Application Data

(60) Division of application No. 15/412,082, filed on Jan. 23, 2017, now Pat. No. 10,383,752, which is a
(Continued)

(51) Int. Cl.
*A61F 2/90*    (2013.01)
*A61F 2/07*    (2013.01)
(Continued)

(52) U.S. Cl.
CPC ................. *A61F 2/90* (2013.01); *A61F 2/07* (2013.01); *A61F 2/95* (2013.01); *A61F 2/06* (2013.01);
(Continued)

(58) Field of Classification Search
CPC .. A61F 2/82; A61F 2/844; A61F 2/852; A61F 2/856; A61F 2/86; A61F 2/88;
(Continued)

(56) References Cited

U.S. PATENT DOCUMENTS 6,258,117 B1    7/2001    Camrud et al.
6,331,188 B1    12/2001   Lau et al.
(Continued)

FOREIGN PATENT DOCUMENTS

CN    103356315 A    10/2013
EP    1295571 A1    3/2003
(Continued)

OTHER PUBLICATIONS

Russian Patent Office, Search Report in Russian Patent Application No. 2017126319 dated Jun. 28, 2019.
(Continued)

*Primary Examiner* — Tan-Uyen T Ho
*Assistant Examiner* — Chima U Igboko
(74) *Attorney, Agent, or Firm* — NK Patent Law

(57) ABSTRACT

An assembly including a deployment device for deploying a stent device into an aorta of a patient is provided. The deployment device includes a rod translatable within an aorta of a patient and a first release wire configured for releasing one or more radially constraining members, wherein the radially constraining members are configured to constrain a diameter of the stent device. The stent device is at least partially permeable and engaged with the deployment device in an initial configuration, wherein a diameter and a length of the stent device in a deployed configuration can be altered by axial translation of the rod and releasing one or more of the radially constraining members by translation of the first release wire.

10 Claims, 25 Drawing Sheets

Related U.S. Application Data continuation of application No. PCT/US2016/012845, filed on Jan. 11, 2016.

(60) Provisional application No. 62/102,094, filed on Jan. 11, 2015, provisional application No. 62/185,750, filed on Jun. 29, 2015, provisional application No. 62/237,531, filed on Oct. 5, 2015, provisional application No. 62/259,045, filed on Nov. 23, 2015.

(51) Int. Cl.
  *A61F 2/95* (2013.01)
  *A61F 2/848* (2013.01)
  *A61F 2/06* (2013.01)
  *A61F 2/966* (2013.01)

(52) U.S. Cl.
  CPC ....... *A61F 2/966* (2013.01); *A61F 2002/8486* (2013.01); *A61F 2002/9505* (2013.01); *A61F 2002/9511* (2013.01); *A61F 2002/9522* (2013.01); *A61F 2230/0067* (2013.01); *A61F 2240/002* (2013.01); *A61F 2250/001* (2013.01); *A61F 2250/0007* (2013.01); *A61F 2250/0039* (2013.01)

(58) Field of Classification Search
  CPC .... A61F 2/885; A61F 2/89; A61F 2/90; A61F 2/91; A61F 2/915; A61F 2/92; A61F 2/93; A61F 2/95; A61F 2/954; A61F 2/966; A61F 2/97; A61F 2002/821; A61F 2002/823; A61F 2002/825; A61F 2002/826; A61F 2002/282; A61F 2002/91508; A61F 2002/91516; A61F 2002/91525; A61F 2002/91533; A61F 2002/91541; A61F 2002/9155; A61F 2002/91558; A61F 2002/91566; A61F 2002/91583; A61F 2002/91591; A61F 2002/9505; A61F 2002/9511; A61F 2002/9528; A61F 2002/9534; A61F 2250/001; A61F 2/962; A61F 2002/91575
  See application file for complete search history.

(56) References Cited

U.S. PATENT DOCUMENTS

| | | | |
|---|---|---|---|
| 6,409,750 | B1 | 6/2002 | Hyodoh et al. |
| 6,656,219 | B1 | 12/2003 | Wiktor |
| 6,695,833 | B1 | 2/2004 | Frantzen |
| 6,723,116 | B2 | 4/2004 | Taheri |
| 6,918,925 | B2 | 7/2005 | Tehrani |
| 7,273,493 | B2 | 9/2007 | Ledergerber |
| 7,488,344 | B2 | 2/2009 | Hartley et al. |
| 8,603,156 | B2 | 12/2013 | Hartley et al. |
| 8,623,067 | B2 | 1/2014 | Berez et al. |
| 8,668,729 | B2 | 3/2014 | Kaufmann et al. |
| 8,945,203 | B2 | 2/2015 | Shalev et al. |
| 9,833,341 | B2 | 12/2017 | Bogenschuetz et al. |
| 10,321,985 | B2 | 6/2019 | Barthold et al. |
| 2002/0058984 | A1* | 5/2002 | Butaric ................ A61F 2/064 623/1.13 |
| 2002/0111666 | A1 | 8/2002 | Hart et al. |
| 2002/0177890 | A1 | 11/2002 | Lenker |
| 2003/0040771 | A1 | 2/2003 | Hyodoh et al. |
| 2004/0176832 | A1* | 9/2004 | Hartley ................. A61F 2/07 623/1.11 |
| 2005/0090834 | A1 | 4/2005 | Chiang et al. |
| 2006/0004433 | A1* | 1/2006 | Greenberg ............ A61F 2/07 623/1.11 |
| 2006/0089704 | A1 | 4/2006 | Douglas |
| 2006/0142835 | A1 | 6/2006 | Spiridigliozzi et al. |
| 2006/0155366 | A1 | 7/2006 | LaDuca et al. |
| 2006/0247760 | A1 | 11/2006 | Ganesan et al. |
| 2009/0099650 | A1 | 4/2009 | Bolduc et al. |
| 2009/0259291 | A1* | 10/2009 | Kolbel .................. A61F 2/07 623/1.13 |
| 2009/0319017 | A1 | 12/2009 | Berez et al. |
| 2010/0049307 | A1 | 2/2010 | Ren |
| 2010/0049313 | A1 | 2/2010 | Alon et al. |
| 2010/0114291 | A1 | 5/2010 | Kolbel et al. |
| 2012/0191174 | A1 | 7/2012 | Vinluan et al. |
| 2012/0323300 | A1 | 12/2012 | Greenberg et al. |
| 2013/0144373 | A1 | 6/2013 | Shahriari |
| 2013/0166015 | A1 | 6/2013 | Roeder |
| 2013/0289713 | A1 | 10/2013 | Pearson et al. |
| 2014/0046428 | A1 | 2/2014 | Cragg et al. |
| 2014/0277348 | A1 | 9/2014 | Roeder |
| 2018/0055664 | A1 | 3/2018 | Bogenschuetz et al. |

FOREIGN PATENT DOCUMENTS

| | | |
|---|---|---|
| JP | 2005270432 A | 10/2005 |
| JP | 2011502628 A | 1/2011 |
| JP | 3173720 U | 2/2012 |
| KR | 20000042899 A | 7/2000 |
| RU | 2508079 C2 | 2/2014 |
| WO | 2001035858 A1 | 5/2001 |
| WO | WO0187180 A2 | 11/2001 |
| WO | 2004030706 A3 | 4/2004 |
| WO | 2007028086 A2 | 3/2007 |
| WO | 2010105195 A2 | 9/2010 |
| WO | 2010150208 A2 | 12/2010 |
| WO | 2012068175 A2 | 5/2012 |
| WO | 2012136984 A1 | 10/2012 |
| WO | 2013026485 A1 | 2/2013 |
| WO | 2013167493 A1 | 11/2013 |

OTHER PUBLICATIONS

Russian Patent Office, Office Action in Russian Patent Application No. 2017126319 dated Jun. 28, 2019.
EPO, Extended European Search Report in European Application No. 16735541.1 dated Jul. 20, 2018, amended claims filed in response thereto, Intention to Grant, and application intended for grant.
Di Bartolomeo, Roberto, et al., Frozen elephant trunk surgery using the E-vita open plus prosthesis, Masters of Cardiothoracic Surgery, Annals of Cardiothoracic Surgery, Sep. 5, 2013, vol. 2, pp. 656-659.
USPTO, Non-Final Rejection in U.S. Appl. No. 15/653,657 dated May 30, 2019.
JPO, Office Action for Japanese Patent Application No. 2018-206631, dated Oct. 23, 2019, 9 pages.
JPO, Office Action in Patent Application No. 2017-536857 dated Nov. 26, 2019.
ISA/KR, International Search Report for International Patent Application No. PCT/US2018/019659, dated Jun. 27, 2018, 5 pages.
ISA/KR, Written Opinion of the International Searching Authority for International Patent Application No. PCT/US2018/019659, dated Jun. 27, 2018, 8 pages.
WIPO, International Preliminary Report on Patentability for International Patent Application No. PCT/US2018/019659, dated Sep. 24, 2019, 9 pages.

* cited by examiner

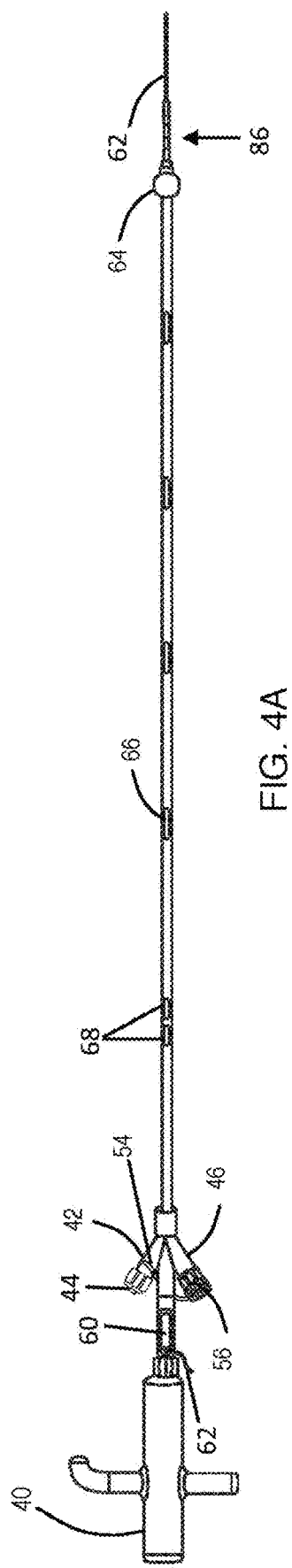
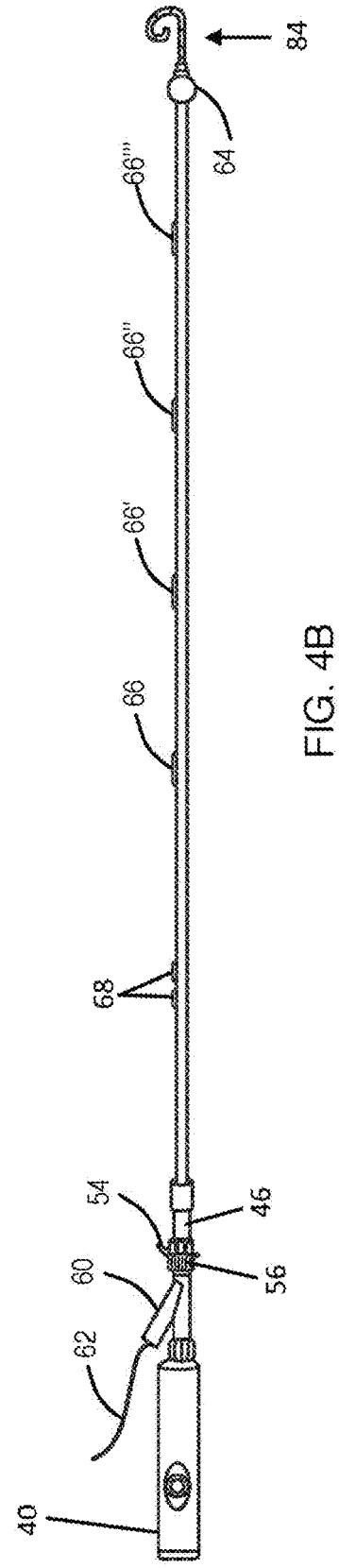

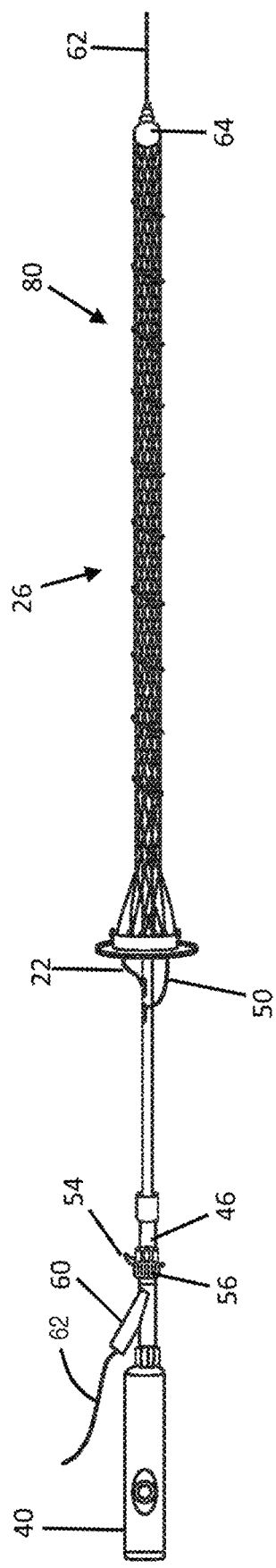

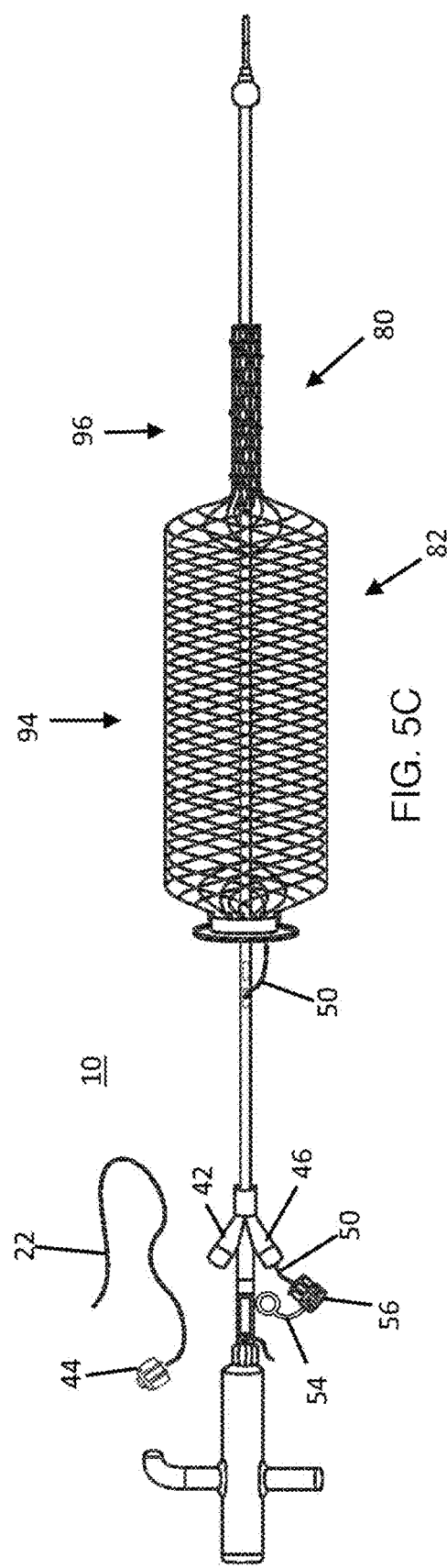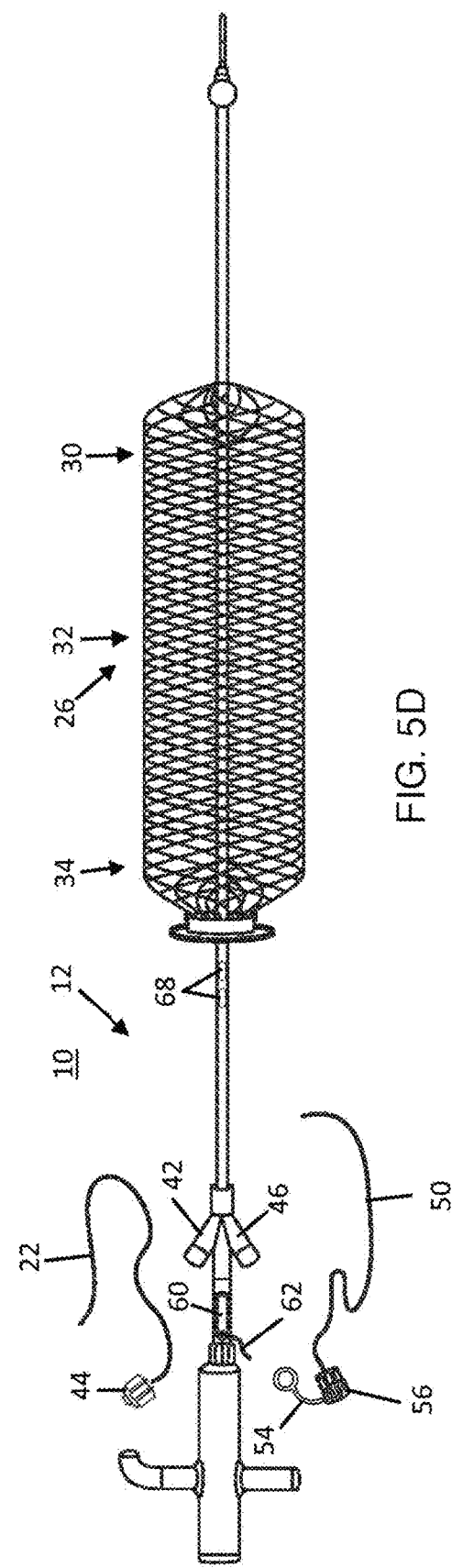

HYBRID DEVICE FOR SURGICAL AORTIC REPAIR CONFIGURED FOR ADAPTABILITY OF ORGANS OF VARIOUS ANATOMICAL CHARACTERISTICS AND METHOD OF USING THE SAME

CROSS-REFERENCE TO RELATED APPLICATIONS

This application is a divisional of U.S. patent application Ser. No. 15/412,082, filed Jan. 23, 2017 and titled "HYBRID DEVICE FOR SURGICAL AORTIC REPAIR CONFIGURED FOR ADAPTABILITY OF ORGANS OF VARIOUS ANATOMICAL CHARACTERISTICS AND METHOD OF USING THE SAME", which is a continuation of PCT Patent Application No. PCT/US16/12845 filed Jan. 11, 2016 and titled "HYBRID DEVICE FOR SURGICAL AORTIC REPAIR CONFIGURED FOR ADAPTABILITY OR ORGANS OF VARIOUS ANATOMICAL CHARACTERISTICS AND METHOD OF USING THE SAME", which claims the benefit of U.S. Provisional Application 62/102,094 filed Jan. 11, 2015 and titled "DEVICE FOR ENDOVASCULAR AORTIC REPAIR CONFIGURED FOR ADAPTABILITY OF ORGANS OF VARIOUS ANATOMICAL CHARACTERISTICS AND METHOD OF USING THE SAME"; claims the benefit of U.S. Provisional Application 62/185,750 filed Jun. 29, 2015 and titled "HYBRID DEVICE FOR SURGICAL AORTIC REPAIR CONFIGURED FOR ADAPTABILITY OF ORGANS OF VARIOUS ANATOMICAL CHARACTERISTICS AND METHOD OF USING THE SAME"; claims the benefit of U.S. Provisional Application 62/237,531 filed Oct. 5, 2015 and titled "HYBRID DEVICE FOR SURGICAL AORTIC REPAIR CONFIGURED FOR ADAPTABILITY OF ORGANS OF VARIOUS ANATOMICAL CHARACTERISTICS AND METHOD OF USING THE SAME"; and claims the benefit of U.S. Provisional Application 62/259,045 filed Nov. 23, 2015 and titled "HYBRID DEVICE FOR SURGICAL AORTIC REPAIR CONFIGURED FOR ADAPTABILITY OF ORGANS OF VARIOUS ANATOMICAL CHARACTERISTICS AND METHOD OF USING THE SAME"; each of which are herein incorporated by reference in their entirety.

TECHNICAL FIELD

The present disclosure relates to a device and method of using the same for open hybrid repair of ascending and arch aneurysms and aortic dissections.

BACKGROUND

Open resection of ascending aneurysms and in particular aortic dissections, carries a high mortality. In type A dissections, the mortality with open repair may reach up to 25%, many patients dying from bleeding complications or cerebral complications associated with using deep hypothermic circulatory arrest (DHCA). The friability of the tissues in these patients is a significant challenge when reconstructing and sewing a graft to the distal ascending aorta and the proximal arch, which in turn increases the duration of DHCA and therefor the complication and mortality rates. Type A dissections typically start in the ascending aorta and propagate distally delaminating the wall of the aorta causing a chronic weakness in the wall that in many cases degenerates into an aneurysm. The intimal flap creates 2 or more pathways of flow called the true (TL) and false lumen (FL). These conditions are effectively treated by surgical resection and replacement of the ascending aorta. However, the delaminated wall of the aorta is typically untreated because of the high risk associated with the additional resection of the aorta distal to the ascending segment. Additionally, the aortic arch of a patient may have variation in size, dimensions and the like. Use of stent portions for being received within the arch are thus constrained by the variations among different aortic arches.

Acute aortic dissections and intramural hematomas (IMH) are caused by an intimal tear or hemorrhage within the aortic wall. This causes delamination and propagation of the intimal flap proximally and distally. The proximal propagation of the intimal flap can cause aortic insufficiency, blockage of coronary arteries, aortic rupture and death. This is prevented by surgical replacement of the ascending aorta. Distal propagation of the intimal flap can cause blockage of important aortic side branches leading to stroke or visceral malperfusion. Typically the pressurized and perfused FL expands and causes the compression of the TL. During the acute phase of the dissection process, the tear causes inflammation of the aortic wall. If the intimal flap is reattached and supported, the inflammation will help in fusing the dissected layers and potentially allow the dissection to cure. This will encourage positive aortic remodeling and exclusion/depressurization of the FL.

Although the technique of ascending aortic replacement has been perfected, currently there are no effective means of reattaching the dissected intimal flap to the aortic wall in the arch and beyond. To address the long term complications attributed to the FL, different devices have been designed but none have been shown to be effective. In addition, some surgeons advocated for additional resection of the aortic arch during the index operation, however the majority of surgeons are reluctant to do so due to an increase in the complexity of the operation and the mortality. Additionally, resection of the arch will not exclude the FL in the remainder of the aorta. The endovascular solutions available for treatment of aortic aneurysms are inadequate for treatment of dissections because their graft coverage fixes their diameter and won't allow for the device to expand freely to re-attach the intimal flap. In addition, the graft coverage will obstruct important aortic side branches perfusing the brain, spinal cord and viscera.

The above challenges may be overcome by the invention disclosed in this application, where the proximal reinforced section of the graft allows for a more secure and hemostatic suture line, the distal stent reinforced graft section allows for future landing zone to implant additional endografts and the intervening braided, uncovered stent portion allows tacking and stabilizing of the aortic tear and the detached intima to the remainder of the aorta without compromising blood flow to the supra-aortic branches, thereby excluding the FL and providing an opportunity for the tear to heal and to cure the dissection.

SUMMARY

According to one or more embodiments, an assembly including a stent device engaged with a deployment device in an initial configuration is provided. The deployment device has a rod translatable within an aorta of a patient and having an operator end and a distal end, and a first release wire configured for releasing one or more radially constraining members constraining the diameter of the stent device. The stent device has a distal portion for being engageably received in the aortic arch of the patient and extending beyond the left subclavian artery when implanted. Further, the stent device has a stent portion fluidly engaged with the distal portion, the stent portion being at least partially permeable and configured to span a portion of the aortic arch to which the brachiocephalic trunk, left common carotid artery, and left subclavian artery attach. Additionally, the stent device includes a proximal portion fluidly engaged with the stent portion. A diameter and a length of the stent device in a deployed configuration can be altered by axial translation of the rod and releasing one or more of the radially constraining members by translation of the first release wire.

According to one or more embodiments, a method of deploying a stent device into an aorta of a patient is provided wherein a stent device is engaged about a rod of a deployment device in an initial configuration. The method includes positioning a distal portion of the stent device at least beyond the left subclavian artery by axially translating a distal end of the rod into the aorta, wherein the stent device further includes a stent portion in fluid engagement with the distal portion and a proximal portion in fluid engagement with the stent portion. The method further includes releasing one or more radially constraining members constraining a diameter of the stent portion and modifying the length and the diameter of the stent device into a deployed configuration by axially translating the rod within the aorta. Additionally, the stent portion is positioned to span and engage a portion of the aortic arch to which the brachiocephalic trunk, the left common carotid artery, and the left subclavian artery attach. Finally, the method includes removing the rod from the aorta of the patient.

BRIEF DESCRIPTION OF THE DRAWINGS

The previous summary and the following detailed descriptions are to be read in view of the drawings, which illustrate particular exemplary embodiments and features as briefly described below. The summary and detailed descriptions, however, are not limited to only those embodiments and features explicitly illustrated.

FIG. 4A is a top view of a deployment device having a linear arrangement of a tip according to one or more embodiments of the present invention.

FIG. 4B is a side view of a deployment device having a non-linear arrangement of a tip according to one or more embodiments of the present invention.

FIG. 4C is a side view of an assembly including a loaded stent device and a deployment device according to one or more embodiments of the present invention.

FIGS. 5A through 5D are top views of a deployment device being used to configure a stent device using release wires according to one or more embodiments of the present invention.

DETAILED DESCRIPTION OF THE DRAWINGS

Figure 1:
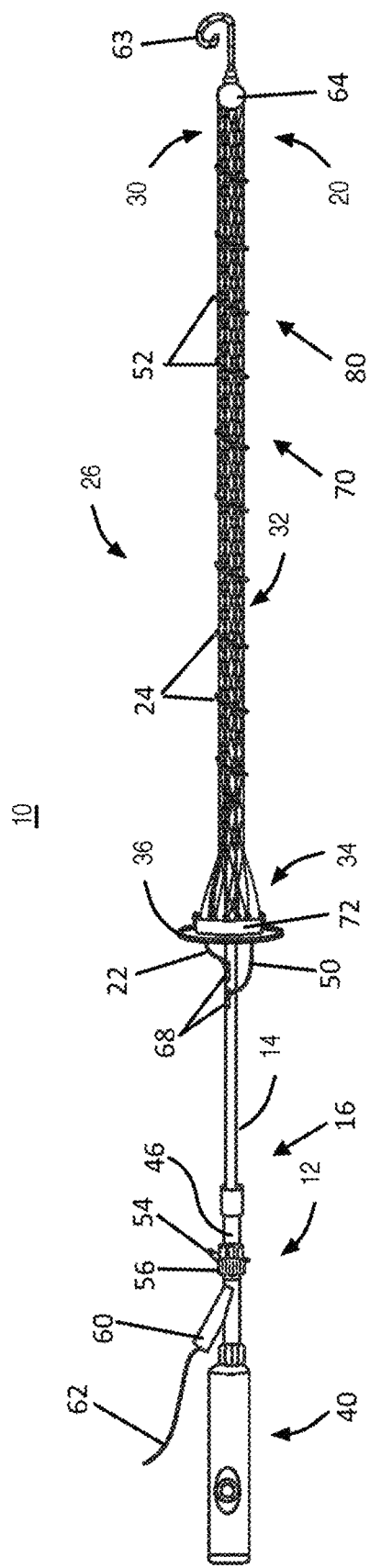
FIG. 1 is a side view of an assembly including a deployment device and a stent device according to one or more embodiments of the present invention.

These descriptions are presented with sufficient details to provide an understanding of one or more particular embodiments of broader inventive subject matters. These descriptions expound upon and exemplify particular features of those particular embodiments without limiting the inventive subject matters to the explicitly described embodiments and features. Considerations in view of these descriptions will likely give rise to additional and similar embodiments and features without departing from the scope of the inventive subject matters. Although the term "step" may be expressly used or implied relating to features of processes or methods, no implication is made of any particular order or sequence among such expressed or implied steps unless an order or sequence is explicitly stated. While the concepts of the present disclosure are susceptible to various modifications and alternative forms, specific exemplary embodiments thereof have been illustrated by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Any dimensions expressed or implied in the drawings and these descriptions are provided for exemplary purposes. Thus, not all embodiments within the scope of the drawings and these descriptions are made according to such exemplary dimensions. The drawings are not made necessarily to scale. Thus, not all embodiments within the scope of the drawings and these descriptions are made according to the apparent scale of the drawings with regard to relative dimensions in the drawings. However, for each drawing, at least one embodiment is made according to the apparent relative scale of the drawing.

Terms representing anatomical references, such as anterior, posterior, medial, lateral, superior, inferior, distal, proximal, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 2:
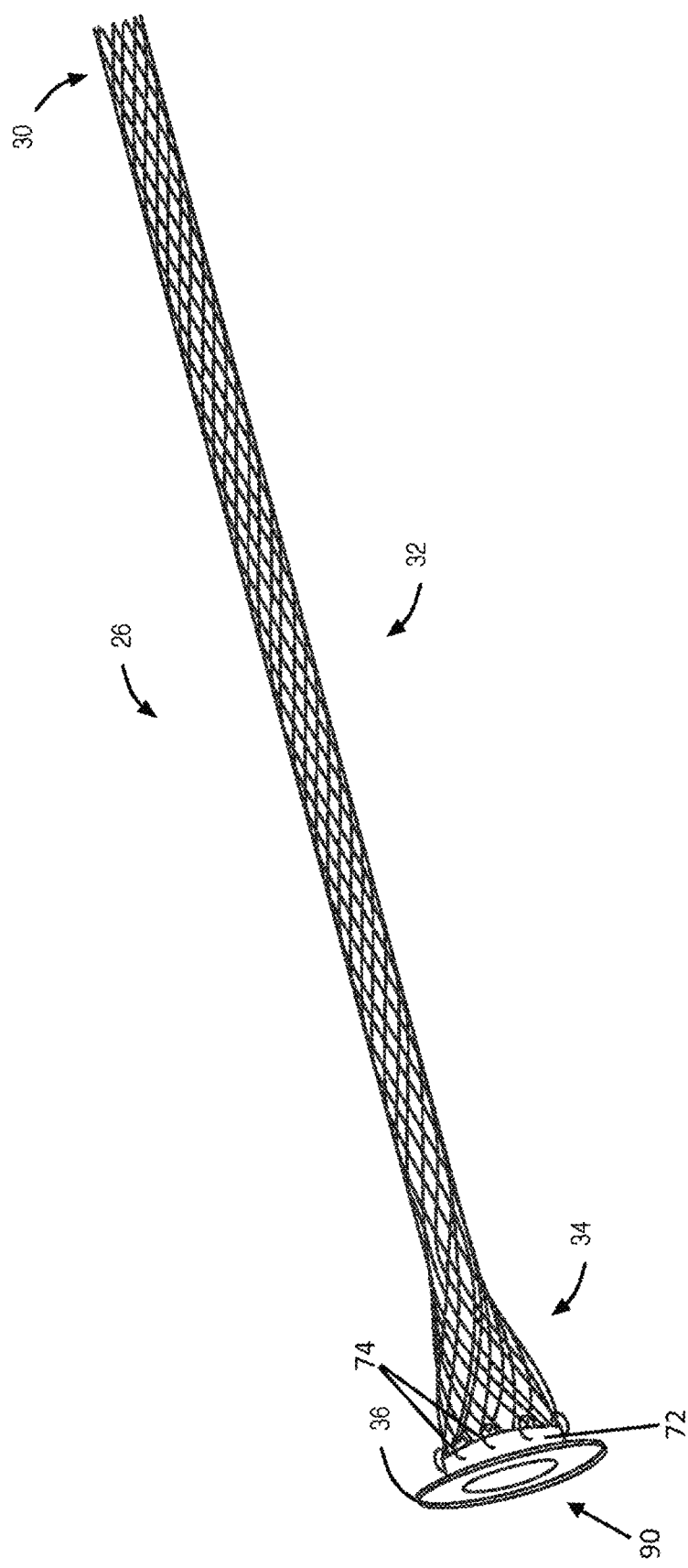
FIG. 2 is a perspective view of a stent device having a proximal portion engaged with a collar according to one or more embodiments of the present invention.
Figure 3:
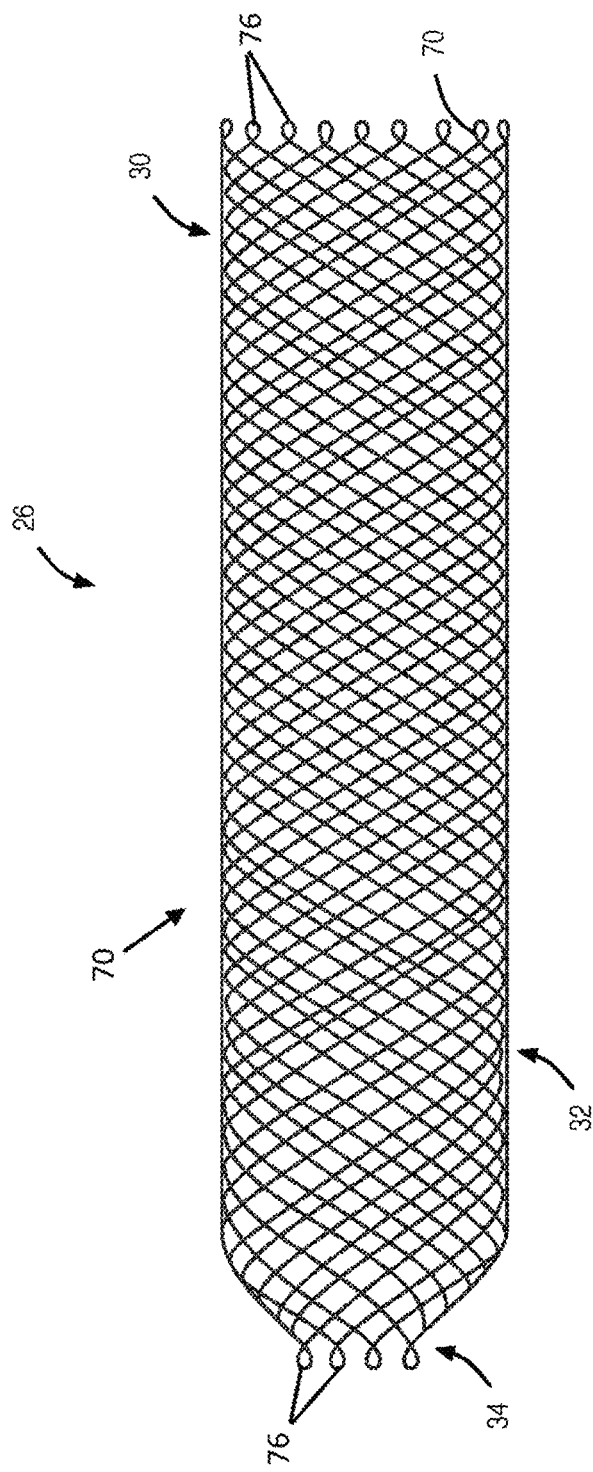
FIG. 3 is a perspective view of a proximal portion, a stent portion and a distal portion of a stent device according to one or more embodiments of the present invention.
Figure 8A:
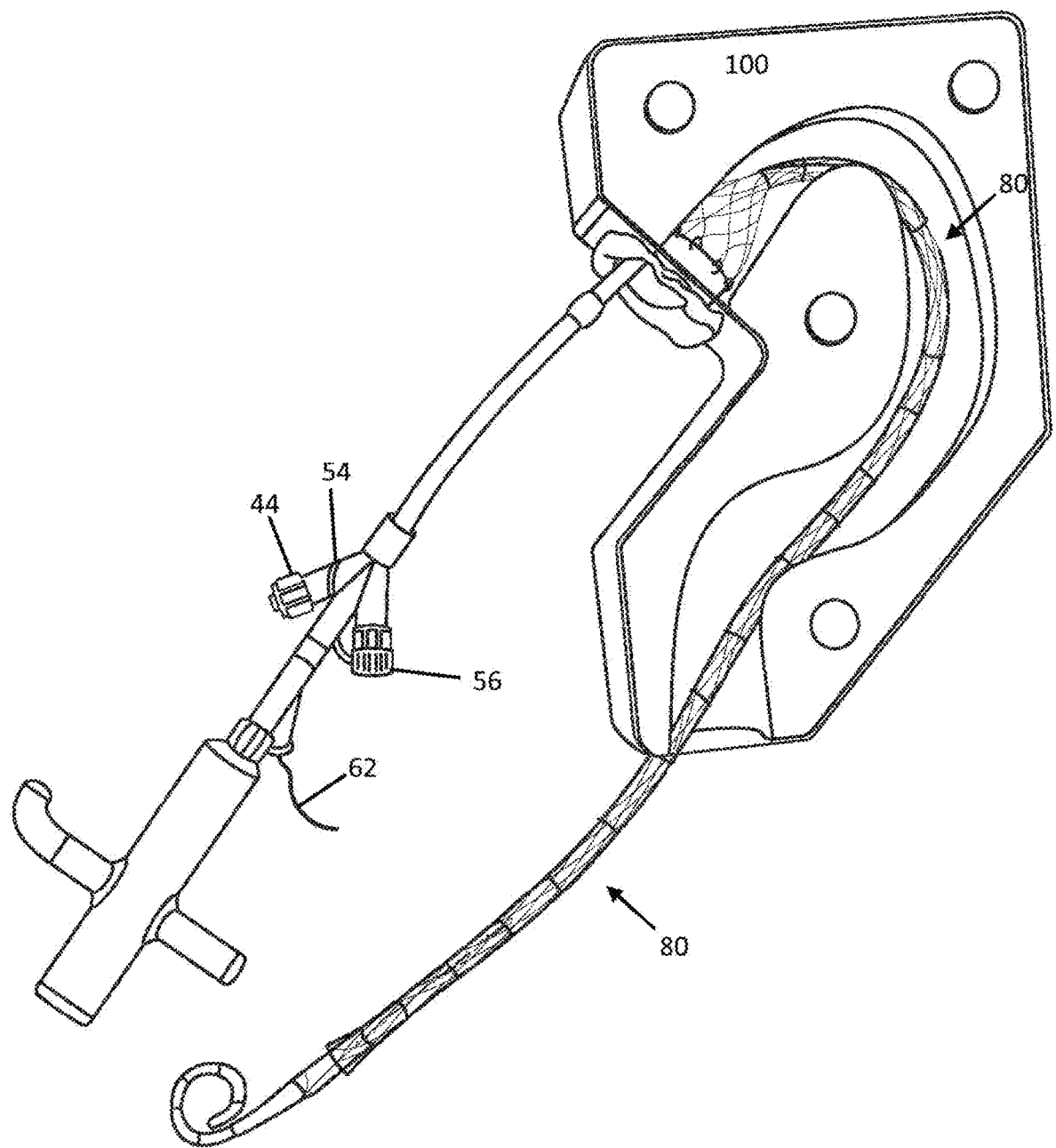
FIGS. 8A through 8H are illustrations of a stent device being deployed within an aorta using a deployment device according to one or more embodiments of the present invention.
Figure 8B:
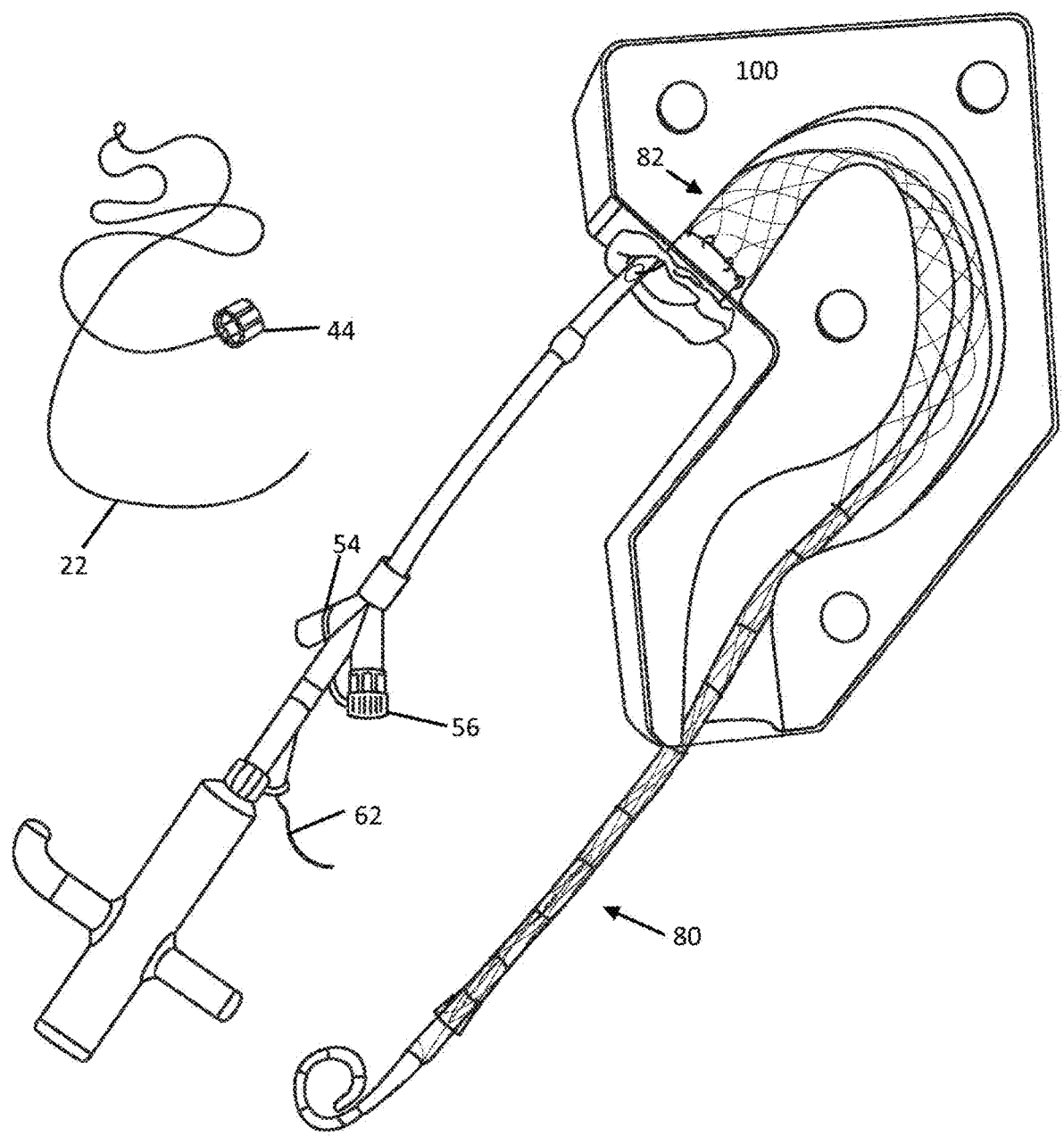
Figure 8C:
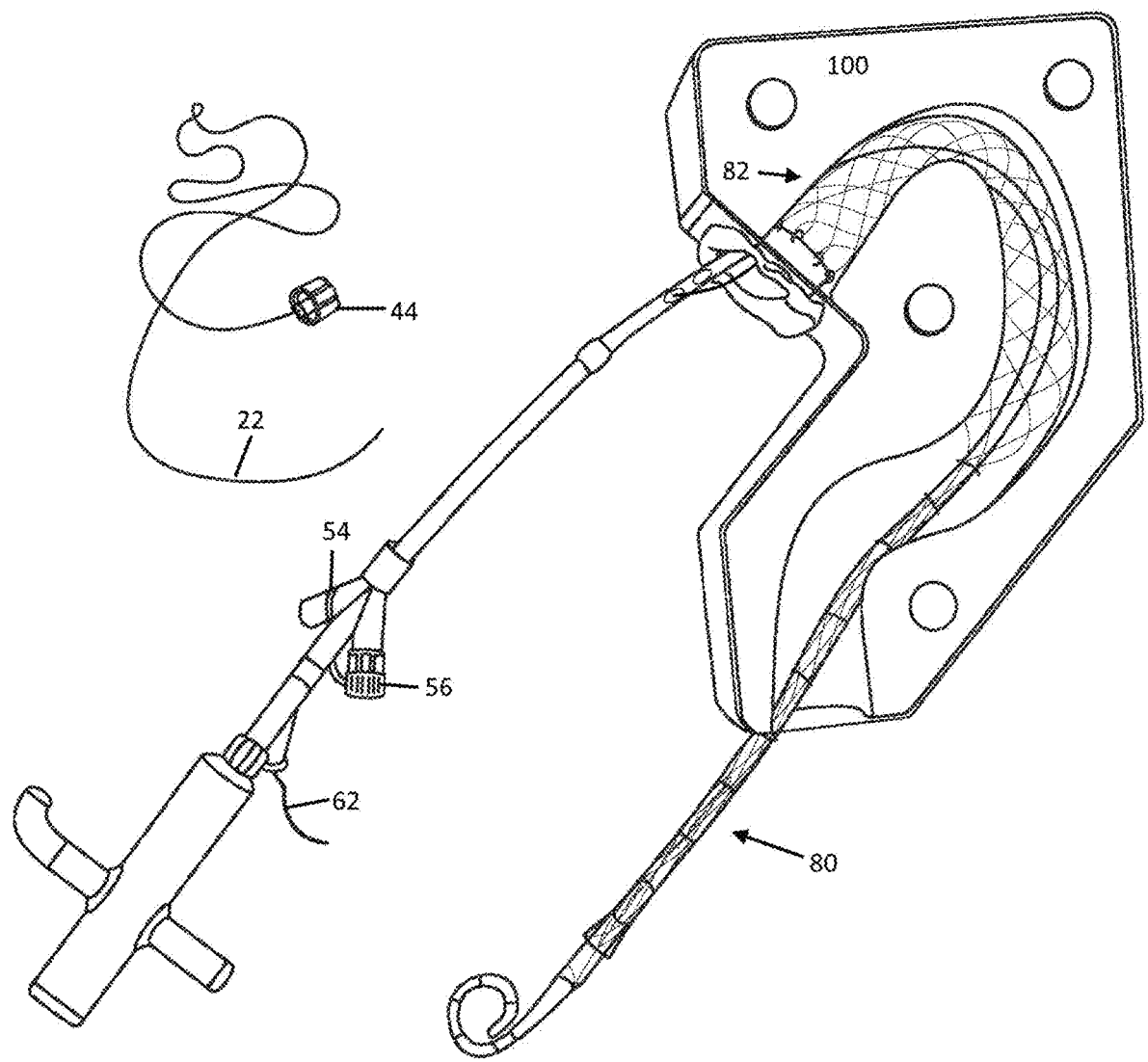

Referring to FIGS. 1, 2, 3, 4A and 4B, an assembly 10 may include a deployment device 12 and a stent device 26, which may be advantageously provided for addressing issues associated with aortic arches of various sizes and dimensions. The stent device 26 of the assembly 10 may be engaged with the deployment device 12 in an initial configuration 80, as depicted in FIG. 1. The stent device 26 may have a distal portion 30 for being engageably received in the aortic arch and descending aorta of the patient and extending beyond the left subclavian artery when implanted, as depicted in FIGS. 8A and 8H. Further, the stent device 26 may have a stent portion 32 fluidly engaged with the distal portion 30, the stent portion 32 being at least partially permeable and configured to span a portion of the aortic arch to which the brachiocephalic trunk, left common carotid artery, and left subclavian artery attach. In this manner, blood flow to each of the brachiocephalic trunk, left common carotid artery, and left subclavian artery flows through the at least partially permeable stent portion 32. As depicted in FIG. 3, a proximal portion 34 of the stent device 26 may also be fluidly engaged with the stent portion 32.

Another unique feature of the stent 26 depicted in FIG. 3 is the tapered terminal end of the stent 26. FIG. 3 depicts an end on the proximal portion 34 being tapered, but some embodiments include the distal portion 30, or both portions 34, 30, being tapered. By designing the stent 26 in a tapered bottle-neck fashion, the stent 26 will be able to be attached to one universal size proximal or distal prosthetic components, such as a proximal graft section 90 or distal graft section 92. The tapering will also expand the stent free areas between the crossing wires of the stent 26 which is important when stents 26 cross major aortic side branches so the blood flow to the branches remain uninhibited. The taper may be created by mechanically narrowing the terminal end of the stent 26 prior to attaching it to the graft component 90, 92. A tapered end could be manufactured in the bottle-neck fashion or it could be created laser cut in a gridded fashion.

This stent device 26 may be designed to be stretched and elongated, with the diameter of the stent device 26 varying while still retaining its structural integrity. In some embodiments, the stent device 26 may be capable of adjusting its length and diameter to the length and diameter of the patient aorta 100 irrespective of size differences between the aorta 100 and the stent device 26. In this manner, the device 26 is conformable to a variety of anatomical features, dimensions, and configurations. Further, the ability for the diameter and the length to vary allows the stent device 26 as a whole to be stretched and elongated on the deployment device 12 and deployed within the aorta 100 while being able to conform its diameter and length to that of the patient's native aortic anatomy. Different parts of stent 26 are capable of adjusting the diameter of the stent 26 to fit the diameter of the aorta 100 in the location the stent 26 is positioned. This means the stent 26 in its entirety is allowed to conform itself to diameter changes of the aorta 100. As an example, if a stent 26 with a resting diameter of 40 mm is implanted by utilizing the assembly 10, the stent component 26 is capable of conforming its diameter to that of the aortic arch and the descending aorta even though the arch diameter is 35 mm and the descending aortic diameter is 20 mm. Conventional stents, stent grafts and assemblies are not capable of such feature. Of course the numbers mentioned in this example are just demonstrative and different ranges of diameter change in the aorta 100 can be accommodated by the assembly 10. In some embodiments, the diameter and length of the stent device 26 in a deployed configuration 82 may be altered by axial translation of a rod 14 of a deployment device 12, and/or by releasing one or more of the radially constraining members 24 by translation of the first release wire 22 of a deployment device 12 (see FIGS. 8A through 8E for a depiction of deployment steps).

Figure 9:
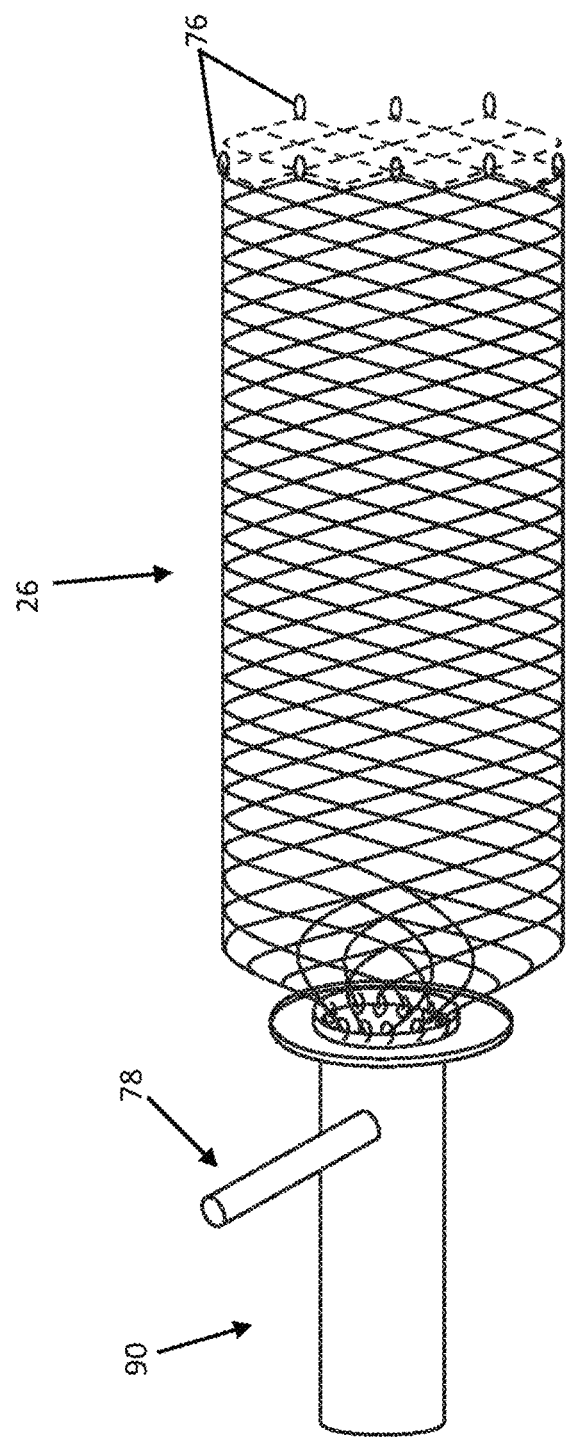
FIG. 9 is a side view of a side arm and a stent device engaged with a collar according to one or more embodiments of the present invention.

The stent device 26 may also be used in a modular fashion with other endovascular devices, graft sections 90, 92 with modular components overlapping and/or engaging in some fashion to treat disease distal or proximal to the stent device 26. As shown in FIGS. 2 and 9, the assembly 10 may include a distinct proximal graft section 90 engaged with the proximal portion 34 of the stent device 26. FIG. 2 depicts the proximal section 90 including a collar 36 engaged with the proximal portion 34, the collar 36 configured for being selectively engaged with the aorta 100 for securing the stent device 26 within the aorta 100. Further, the collar 36 may define a cylindrical component 72 for engaging the proximal portion 34. The cylindrical component may be at least 5 mm in length and can terminate at the level of the collar or extend beyond the level of the collar. This combination of collar and cylindrical component can be used with all stent and graft combinations described in FIGS. 12A through 12D. The collar 36 may measure over 20 mm in diameter and can be fit to use with practically all diameters of aorta 100 treated. This collar 36 may be anastomosed to the transected aorta 100 and can be used similar to a washer to buttress and strengthen the connection between assembly 10, aorta 100 and, for example, any polyester graft that the ascending aorta is typically replaced with.

Examples of other endovascular devices or stents are found in related U.S. patent application Ser. No. 13/706,896 filed on Dec. 6, 2012 and titled "Device for Endovascular Aortic Repair and Method of Using the Same", now U.S. Pat. No. 8,940,040, which is incorporated by reference herein in its entirety.

Figure 10A:
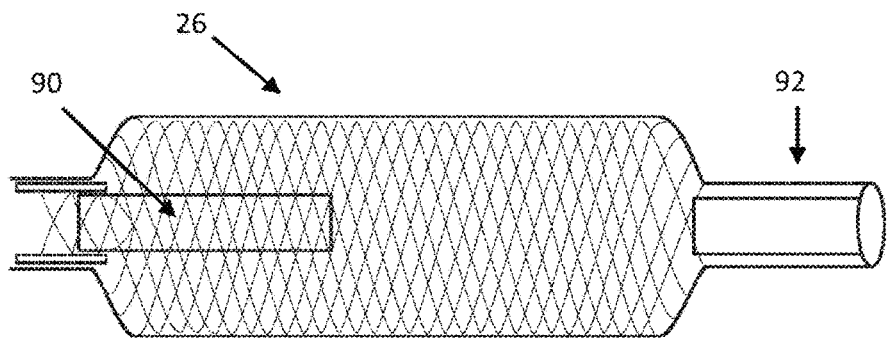
FIG. 10A is an illustration of a proximal graft section inverted within a stent device, which is further engaged with a distal graft section, according to one or more embodiments of the present invention.
Figure 10B:
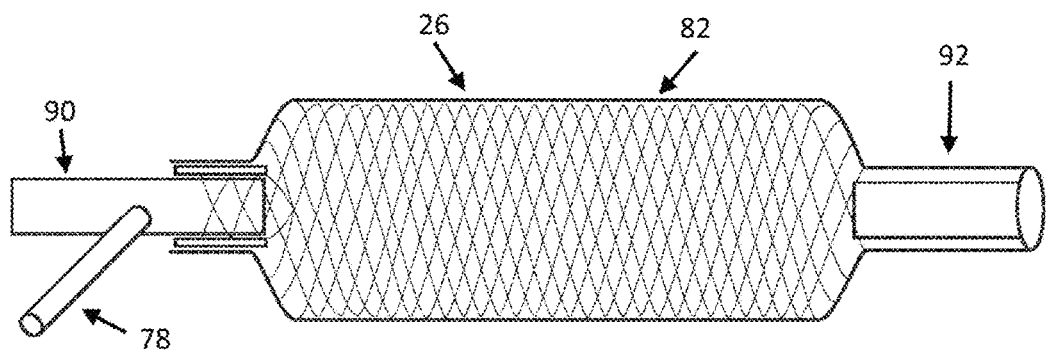
FIGS. 10B and 10C are illustrations of a stent device having a varying diameter and length and engaged with a proximal graft section and a distal graft section according to one or more embodiments of the present invention.
Figure 10C:
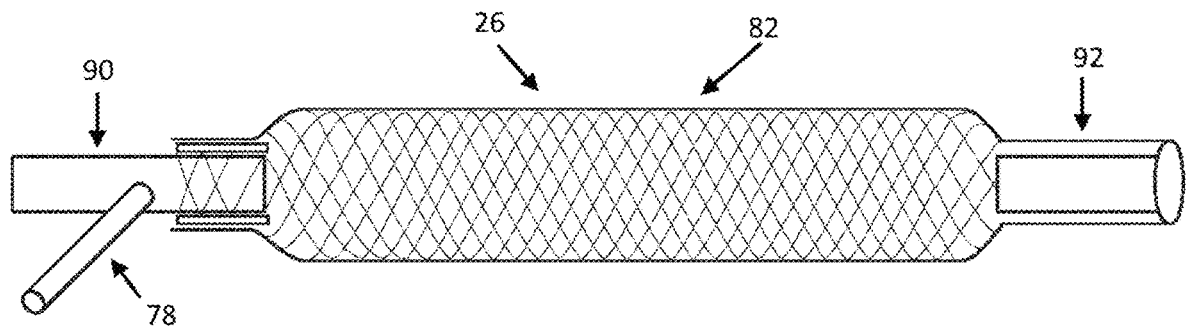

Referring to FIGS. 10A through 10C, the assembly 10 may include a proximal graft section 90 engageable with the proximal portion 34 on one end and with the aorta 100 or another stent on another end. The collar 36 may be donut shaped, as illustrated or take on any appropriate shape or configuration, and may have a diameter of at least 20 mm. In some embodiments, engagement on either end of the proximal graft section 90 may be effectuated using stiches or sutures 74. In at least one embodiment, the proximal graft section 90 may have a diameter of between about 10 mm and 50 mm. As is depicted in FIG. 9, the proximal graft section 90 may define a side arm 78 for providing access with the proximal section 90 and/or stent device 26 for performing bypasses to the supra-aortic branches or for connecting the patient to cardiopulmonary bypass. In some embodiments the side arm 78 may be about 8 mm or larger in diameter. The side arm 78 may be sewn shut in operation or omitted all together if not desired. In some embodiments, the proximal graft section 90 may be inverted into a portion of the stent device 26 for easier delivery, as illustrated in FIG. 10A. A stitch 74 may be attached to the proximal graft section 90 for aiding in pulling the section 90 out of the stent device 26 during or after deployment. When comparing FIGS. 10B and 10C, one notices that when the stent device 26 is elongated, the diameter of the stent device 26 reduces. Similarly, as the length of the stent device 26 is shortened, the diameter increases.

Figure 12A:
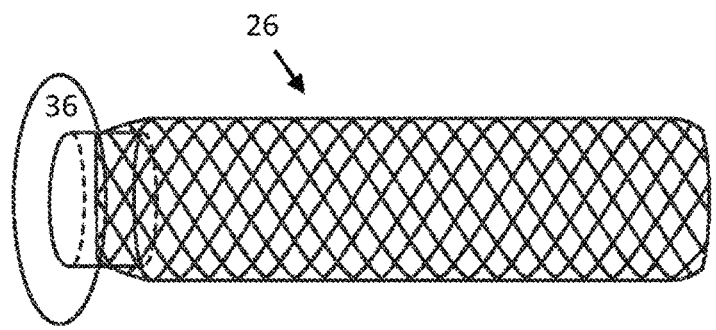
FIG. 12A is an illustration of a stent device engaged with a proximal graft section portion having a collar according to one or more embodiments of the present invention.
Figure 12B:
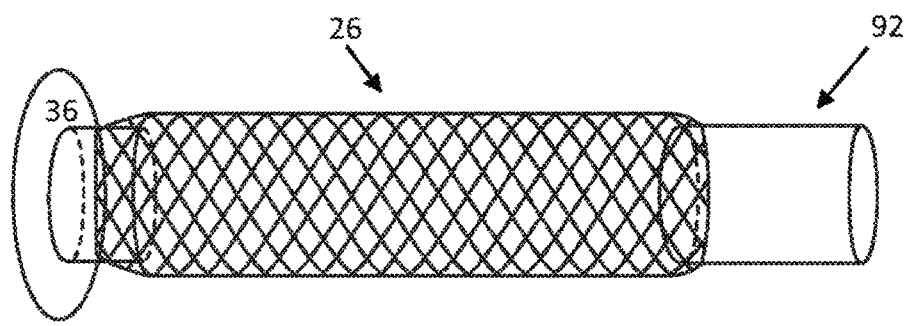
FIG. 12B is an illustration of a stent device engaged with a proximal graft section and a distal graft section according to one or more embodiments of the present invention.
Figure 12C:
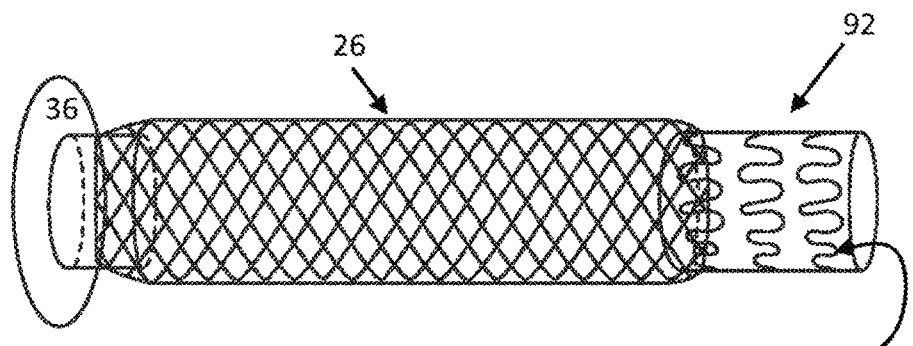
FIG. 12C is an illustration of a stent device engaged with a proximal graft section and a distal graft section having an external or internal support frame according to one or more embodiments of the present invention.
Figure 12D:
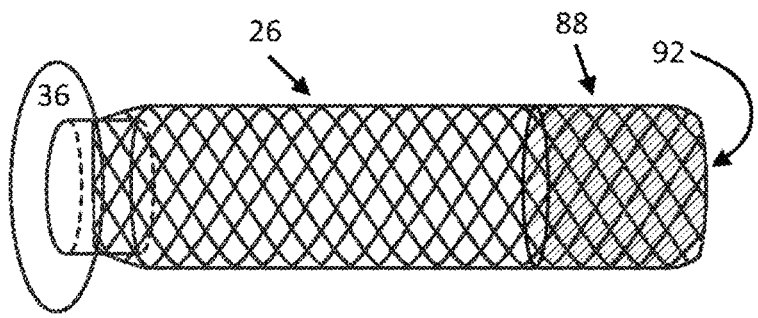
FIG. 12D is an illustration of a stent device engaged with a proximal graft section and a distal graft section externally supported by the stent device frame according to one or more embodiments of the present invention.

The assembly 10 may include a distinct distal graft section 92 engaged with the distal portion 30 of the stent device 26. FIG. 12A depicts an assembly 10 which does not include a distal graft section 92. The distal graft section 92 may be engageably received in a descending aorta of a patient beyond the left subclavian artery. Similar to the proximal graft section 90, the distal graft section 92 may serve as a docking station for modular implantation of other endovascular stents, grafts and/or devices in a modular fashion. The distal graft section 92 may be at least 1 cm in length and made of polyester, PTFE or any other impermeable biologically acceptable prosthetic material and may be a) unsupported, b) supported on its external or internal surface by metallic support frames and stents made of memory shape wire, stainless steel or other alloys and polymers, and/or c) be secured to the internal surface of the distal portion 30 of the stent device 26. FIG. 12B depicts an unsupported distal graft section 92. FIG. 12C illustrates a distal graft section 92 externally supported by a support frame 88. FIG. 12D reveals a distal graft section 92 externally supported by a support frame 88, which, in some embodiments, could be an extension of the distal portion 30 of the stent device 26.

The connection between the graft sections 90, 92 and the stent device 26 may be secured with stitches 74, clips or mechanical fasteners. In some embodiments, the stent device 26 may include eyelets 76 on either the proximal portion 34 and/or distal portion 30 for engaging the stent device 26 with the graft sections 90, 92, or, alternatively, with an anatomical feature of the patient. For example, referring to FIG. 9, the distal portion 30 of the stent device 26 may include eyelets 76 for engaging the aorta 100 or a distal graft section 92. The eyelets 76 may be formed of a contiguous portion of the stent device 26, such as the wire forming the braided stent member 70. Further, the eyelets 76 may provide an anchor point for controlling an end of the graft 90, 92 and/or the stent device 26, as is described in more detail infra.

The stent device 26 and/or the graft sections 90, 92, or portions thereof, may be permeable or impermeable and include a prosthetic material such as polyester, polytetrafluoroethylene (PTFE) or expanded PTFE, or include other suitable biological compatible fluid impermeable material(s). The stent device 26 and/or the graft sections 90, 92, or portions thereof, may be reinforced on their external or internal surface with polymeric scaffold or stent wire scaffold such as z-stent, m-stent, circular or saddle shaped stent, laser cut stents with a gridded pattern, or a braided stent member 70. Further, the stent device 26 may be covered with an impermeable material, such as an impermeable graft section 90, 92, or remain uncovered. The braided stent member 70 may be formed by two or more wires or wire frames, or may be formed by a single continuous braided wire frame. Alternatively, a biodegradable scaffold may allow the stent device 26 and/or graft sections 90, 92 to serve its function in the aorta 100 until the delaminated aorta 100 is healed. Once the aorta 100 is healed, the stent device 26 may be auto-degraded leaving no foreign material behind. In some embodiments the proximal graft section 90 and/or distal graft section 92 may be omitted (e.g., see FIG. 3).

Figure 5A:
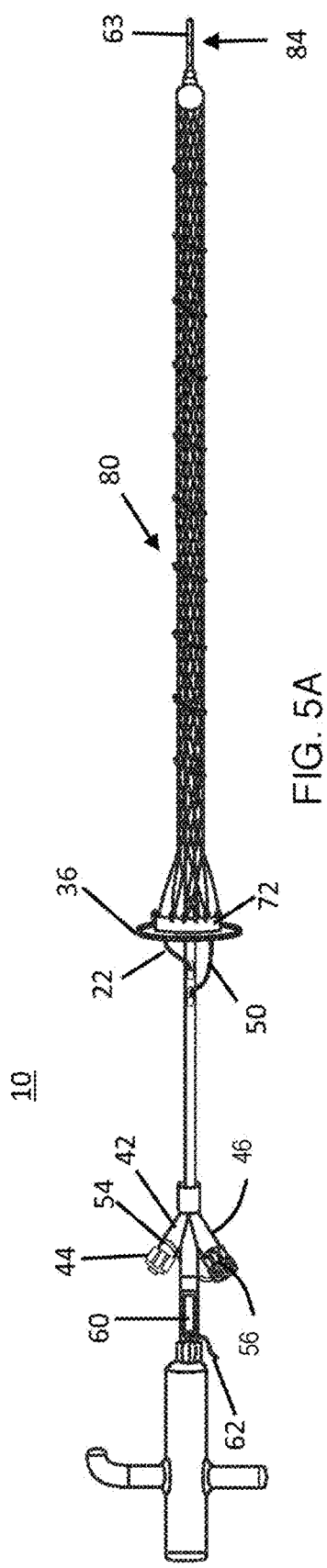
Figure 5B:
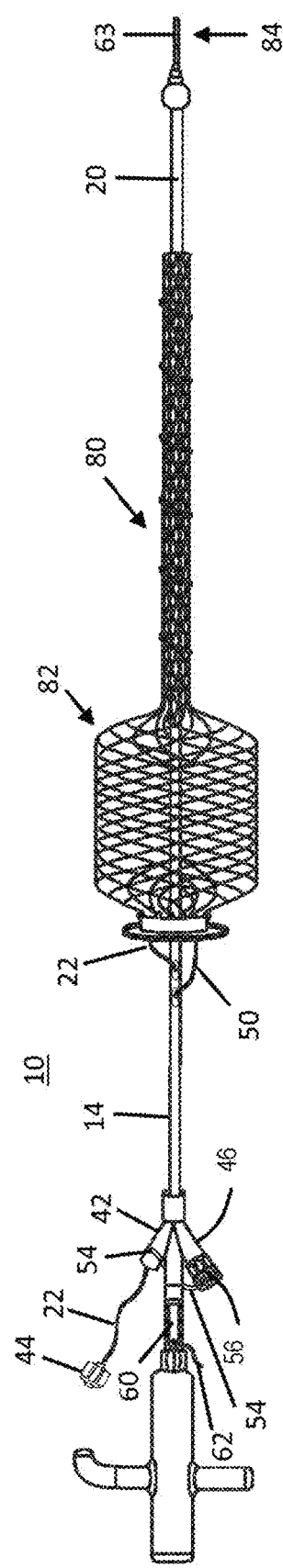
Figure 7A:
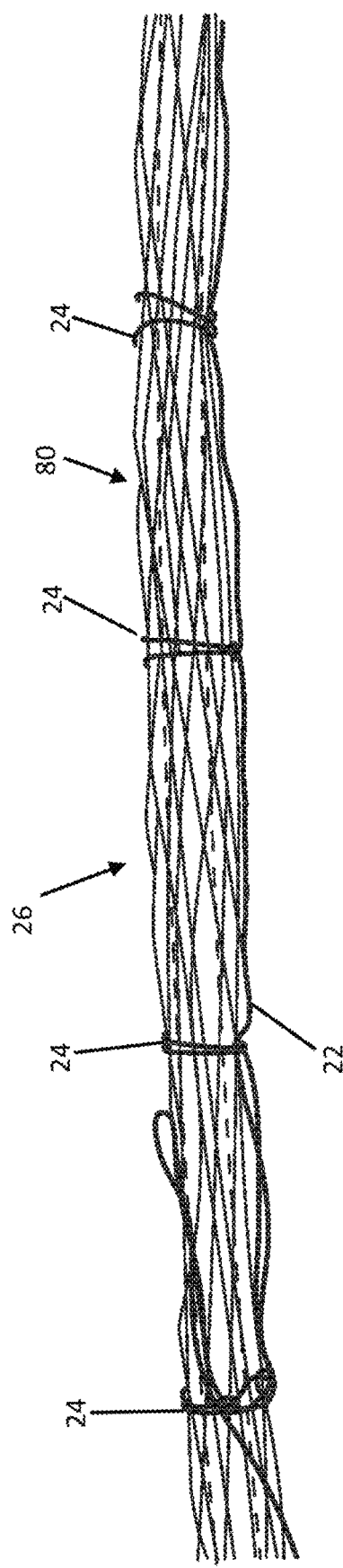
FIGS. 7A and 7B are side views of at least one release wire defining radially constraining members constraining a stent portion according to one or more embodiments of the present invention.
Figure 7B:
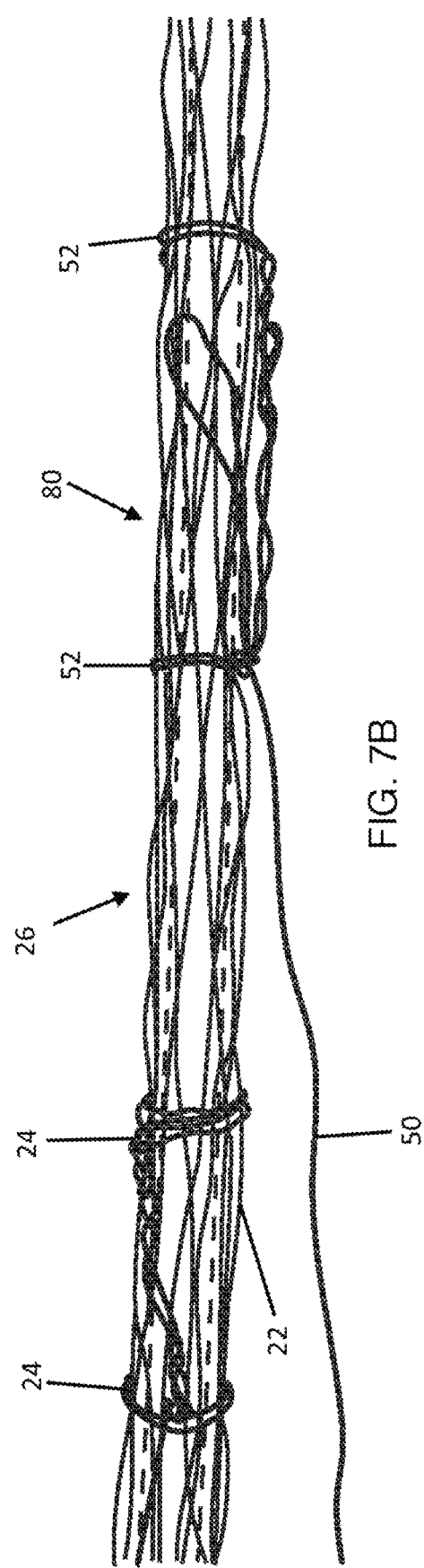

As noted supra, the assembly 10 may include a deployment device 12 for deploying the stent device 26 into the aorta 100 of a patient. In some embodiments, the deployment device 12 may have a first release wire 22 configured for releasing one or more radially constraining members 24 which may be configured to constrain a diameter of the stent device 26 (e.g., see FIGS. 5A, 7A and 7B). The deployment device 12 may define a first outlet 42 from which the first release wire 22 extends. The first release wire 22 may be configured for releasing the one or more radially constraining members 24 (see FIG. 5B). A first cap 44 selectively receivable by the first outlet 42 may be provided. The first release wire 22 may be engaged with the first cap 44 so that translation of the first cap 44 also translates the first release wire 22.

In additional embodiments, the deployment device may also have a second release wire 50 configured for releasing additional one or more radially constraining members 52 which may be configured to constrain a diameter of the stent device 26. The deployment device 12 may define a second outlet 46 from which a second release wire 50 extends. The second release wire 50 may be configured for releasing additional one or more radially constraining members 52. A second cap 56 selectively receivable by the second outlet 46 may be provided. The second release wire 50 may be engaged with the second cap 56 so that translation of the second cap 56 also translates the second release wire 50. In some embodiments, as is depicted in FIG. 5C, partial translation of the second release wire 50 may release a portion of the additional one or more radially constraining members 52. Once the first and second release wires 22, 50 are fully translated, as is illustrated in FIG. 5D, the entire stent device 26 expands to its deployed configuration 82.

Figure 6A:
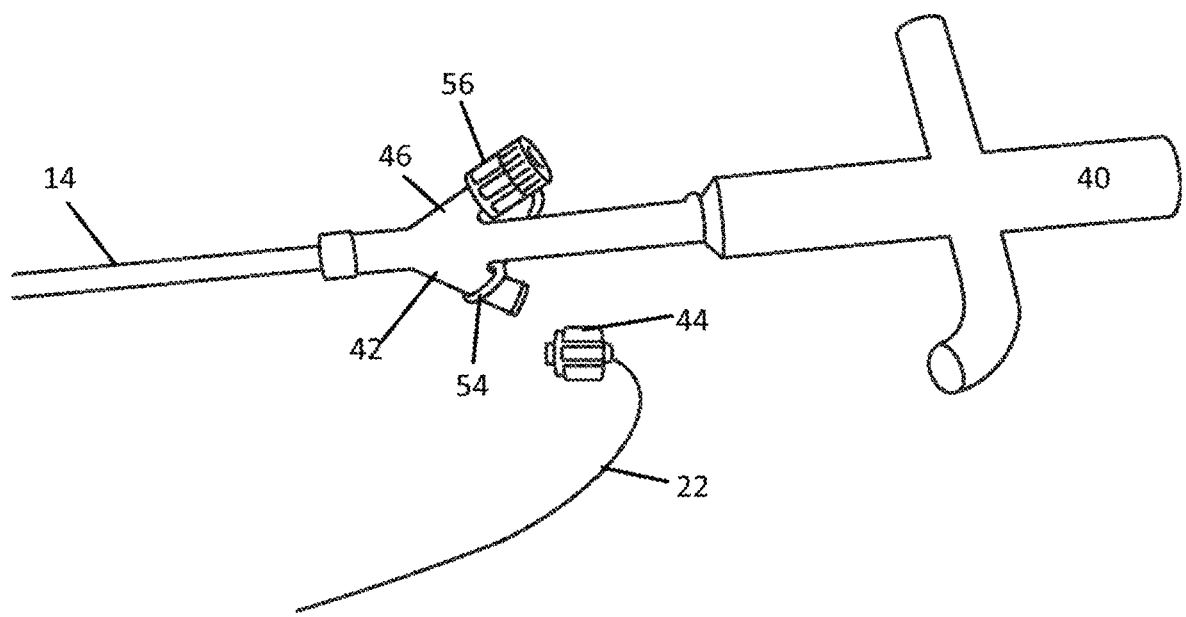
FIGS. 6A and 6B are perspective views of a safety pin being used with the caps of release wires according to one or more embodiments of the present invention.
Figure 6B:
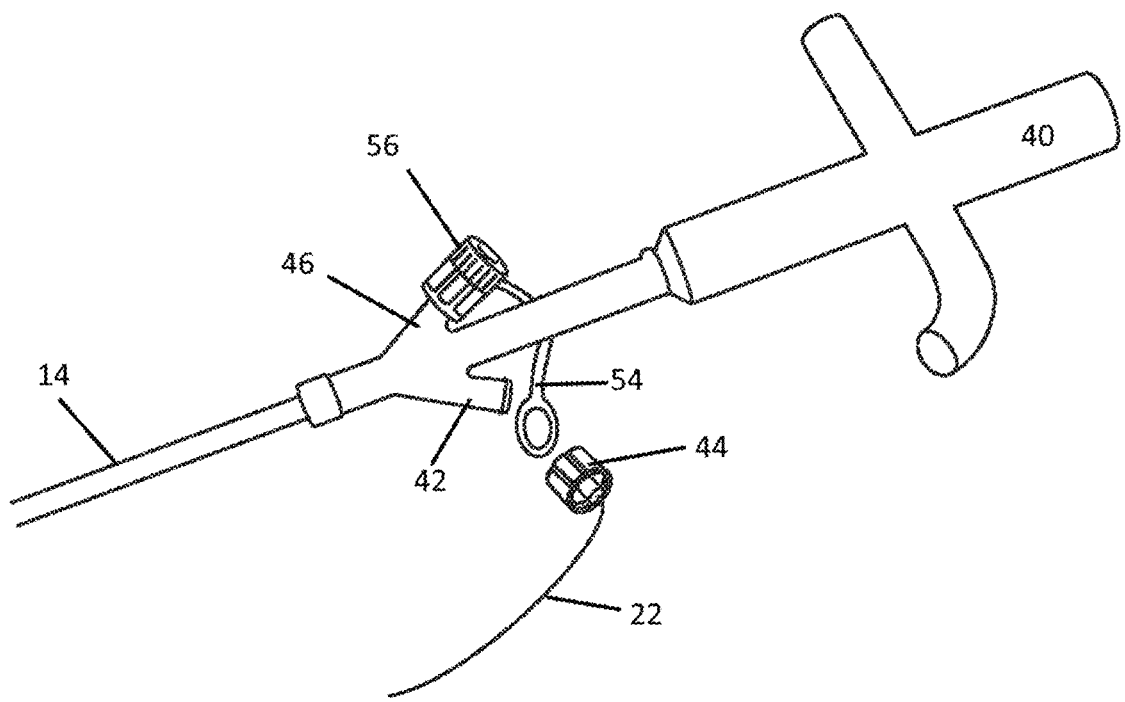

In other embodiments, as depicted in FIGS. 6A and 6B, a safety pin 54 may extend between a first cap 44 selectively receivable by the first outlet 42 and a second cap 56 selectively receivable by the second outlet 46 such that the second cap 56 cannot be disengaged without first disengaging the first cap 44 or, alternatively, by severing the safety pin 54.

Referring again to FIGS. 5A through 5D, the one or more radially constraining members 24 may be configured to release a first segment 94 of the stent device 26, and the additional one or more radially constraining members 52 may be configured to release a second segment 96 of the stent device 26.

As described supra, the stent device 26 of the assembly 10 may be positioned about a rod 14 of the deployment device 12 in an initial configuration 80 (e.g., see FIG. 4C). The rod 14 may be translatable within an aorta 100 of a patient. The rod 14 may have an operator end 16 for engaging a handle assembly 40 of the deployment device 12 and a distal end 20 for placement within the patient. The handle assembly 40 may provide for axial translation of the rod 14.

Referring to FIGS. 4A and 4B, the rod 14 may define one or more protrusions 66, 66', 66", 66''' extending therefrom that are spaced-apart relative to one another. These protrusions 66, 66', 66", 66''' act to slow translation of the stent device 26 for controlling a deployment speed. Further, the rod 14 may include one or more apertures 68 for permitting translation of the one or more release wires 22, 50 therethrough. As is illustrated, the deployment device 12 may define a third outlet 60 through which a guidewire 62 extends. The guidewire 62 may extend through the third outlet 60 and along the length of the rod 14 to a tip 63 defined by the distal end 20 of the rod 14. The rod 14 may define a tip 63 on the distal end 20 that has an initially non-linear arrangement 84 (see FIG. 4B). Advancement of the guidewire 62 through the tip 63 may cause the tip 63 to define a linear arrangement 86 (see FIG. 4A). Additionally, the rod may define a stop member 64 on its distal end 20 for prohibiting movement of the stent device 26 therebeyond. FIG. 4C illustrates a deployment device 12 having a guidewire 62 extending distally therefrom.

Figure 11A:
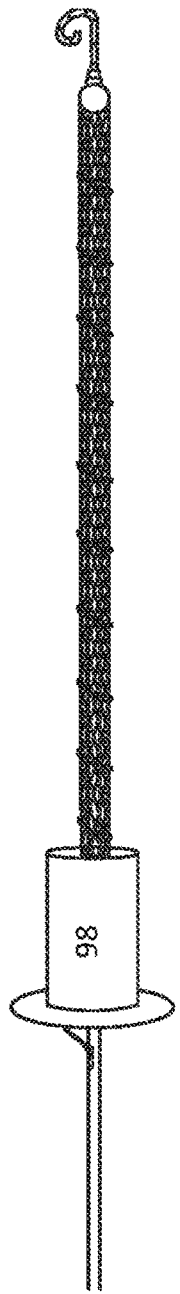
FIGS. 11A through 11C are side views removing a proximal protective member from engagement with a proximal graft portion according to one or more embodiments of the present invention.
Figure 11B:
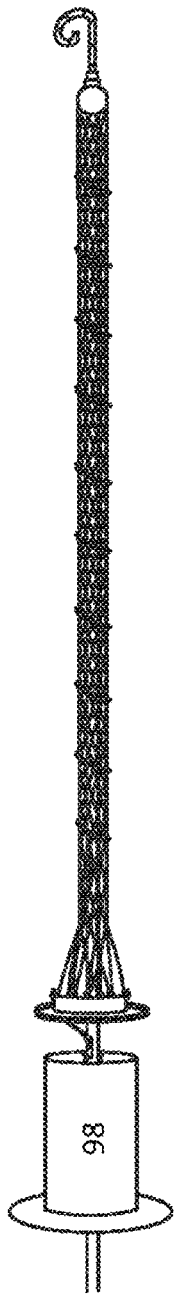
Figure 11C:
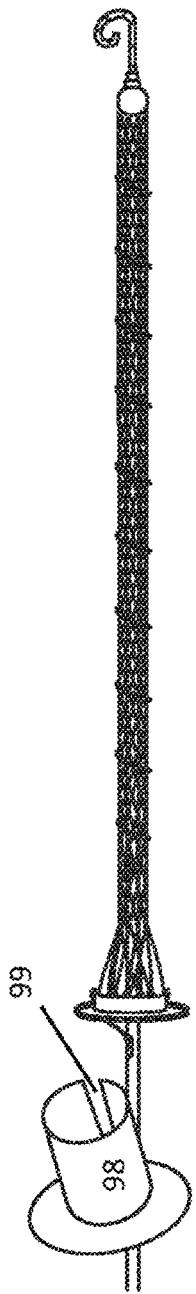

As is illustrated in FIGS. 11A through 11C, a deployment device 12 may include a proximal protective member 98 for engaging the proximal graft section 90 of the stent device 26 for constraining the expansion of the stent device 26 radially and protecting the graft section 90 when in storage or use. Additionally the proximal protective member 98 reduces the profile of the graft section 90 of the assembly 10, making the introduction of the assembly 10 into the aorta 100 easier. The proximal protective member 98 may be removed by axially translating the member 98 and sliding the rod 14 through the transverse slit 99 of the member 98.

Figure 13:
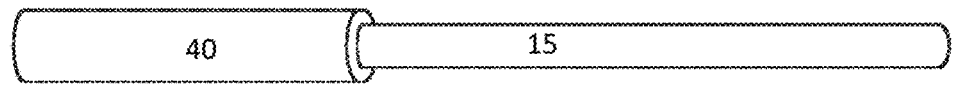
FIG. 13 is an illustration of a deployment device having a handle assembly and a base according to one or more embodiments of the present invention.
Figure 14:
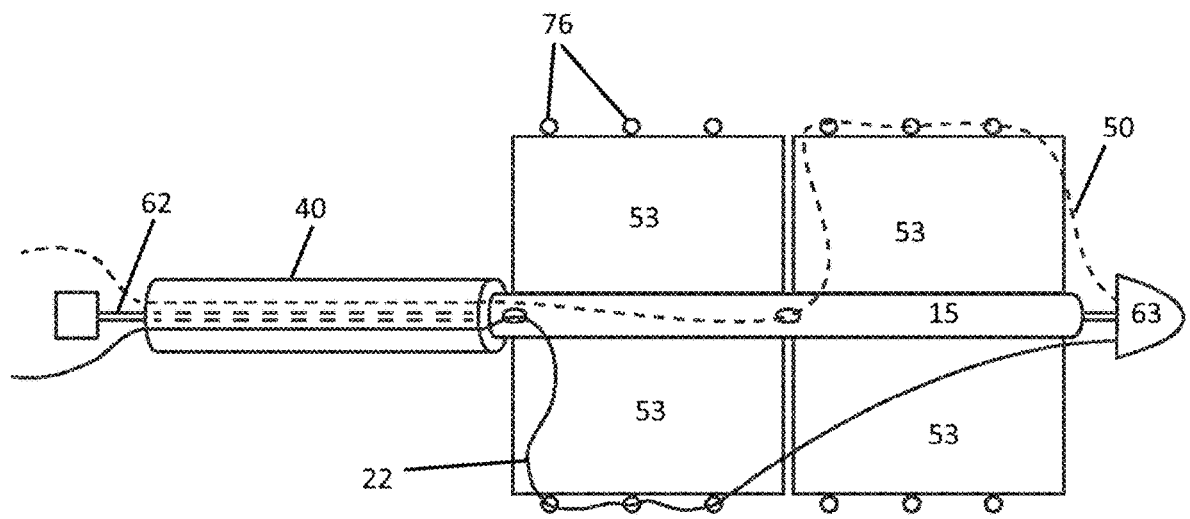
FIG. 14 is an illustration of a deployment device having a handle assembly, a base, release wires and sheaths according to one or more embodiments of the present invention.
Figure 15:
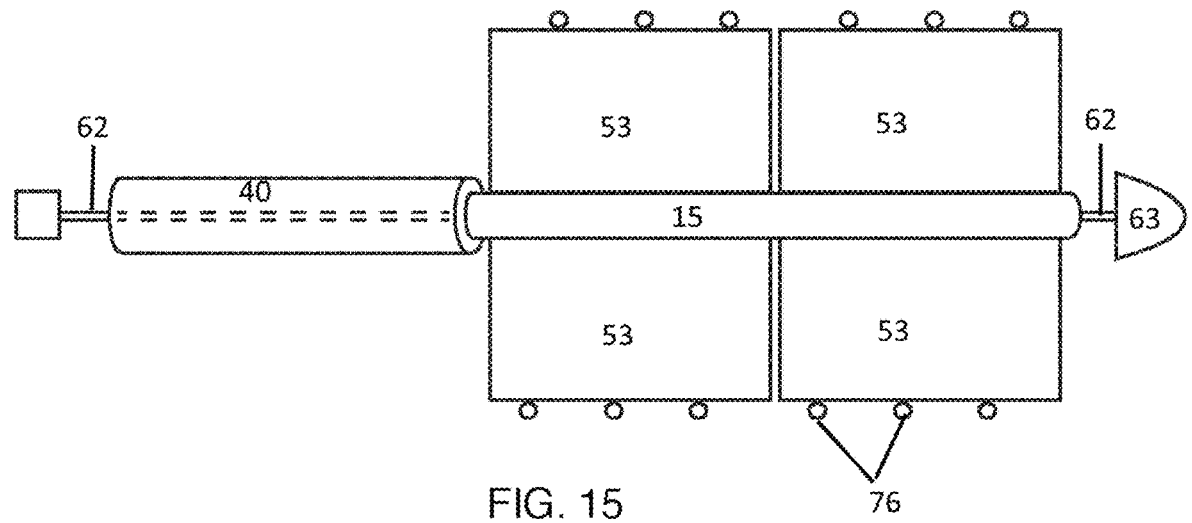
FIG. 15 is an illustration of a deployment device having a rod, a guidewire and sheaths according to one or more embodiments of the present invention.
Figure 16A:
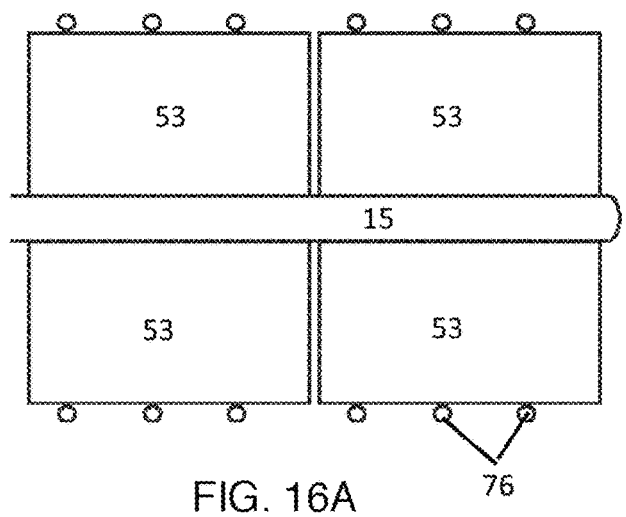
FIGS. 16A and 16B are illustrations of a sheath for folding around a base of a deployment device according to one or more embodiments of the present invention.
Figure 16B:
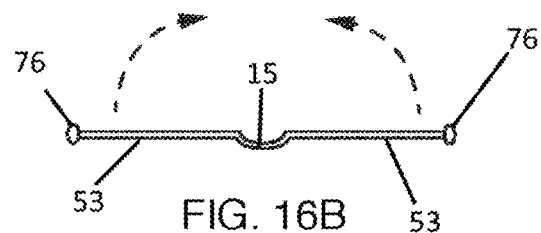

FIGS. 13 through 19 depict alternative embodiments of a deployment device 12 of an assembly 10. As shown in FIG. 13, the deployment device 12 may include a base 15 and a handle assembly 40. The handle assembly 40 may include any of the features described herein. FIG. 14 illustrates one or radially constraining members 24 and additional one or more radially constraining members 52 engaged with the base 15 and extending therefrom. As illustrated, the radially constraining members 24, 52 may be sheaths 53 having eyelets 76 for constraining a stent device 26 therewithin, as is illustrated in FIGS. 15, 16A and 16B.

The sheaths 53 may be comprised of PTFE, ePTFE, or other biologically acceptable materials. The sheath(s) 53 may be crescent shaped, attached at the bottom to the base 15 of the delivery device 12. Alternatively, the sheath(s) 53 may be circular and embrace the base 15 of the delivery system 12. On the upper surface the sheath(s) 53 may be divided by a longitudinal slit 55. Each edge of the slit 55 may be equipped with the eyelets 76 for passage of the release wires 22, 50. After the stent device 26 is loaded within the sheath(s) 53, the passage of release wires 22, 50 through the eyelets 76 will enable the sheath(s) 53 to be closed for containing the stent device 26 therein. The sheaths 53 may operate independently of each other for allowing sequential deployment of the stent device 26.

FIG. 15 illustrates the deployment device 12 further including a guidewire 62 extending from the handle assembly 40 along the length of the base 15 through a rod 14 to a tip 63. The rod 14 may include any of the features described herein. For example, axial translation of the guidewire 62 may be effected through axial translation of the handle assembly 40, thereby translating the tip 63 within the aorta 100. The tip 63 may include an eyelet 76 or some other engagement mechanism for engaging or permitting pass through of at least one release wire 22, 50. The tip 63 may be olive shaped or may have any of the other features described herein.

Figure 17A:
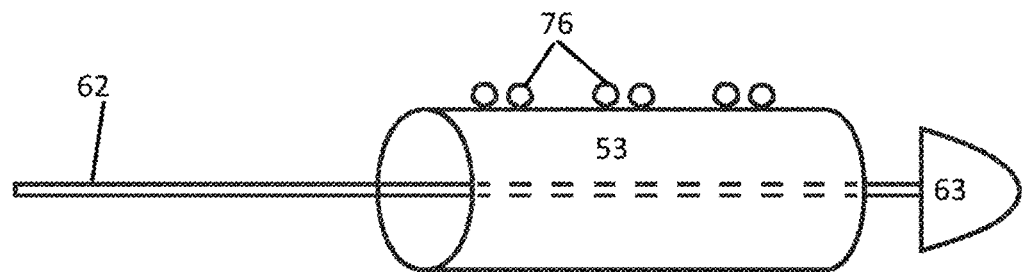
FIGS. 17A and 17B are illustrations of staggered sheaths of a deployment device constraining a stent device according to one or more embodiments of the present invention.
Figure 17B:
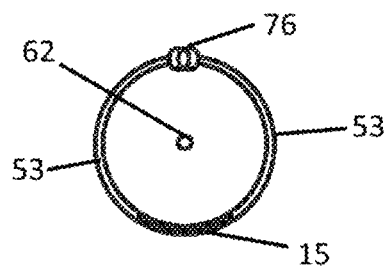
Figure 18A:
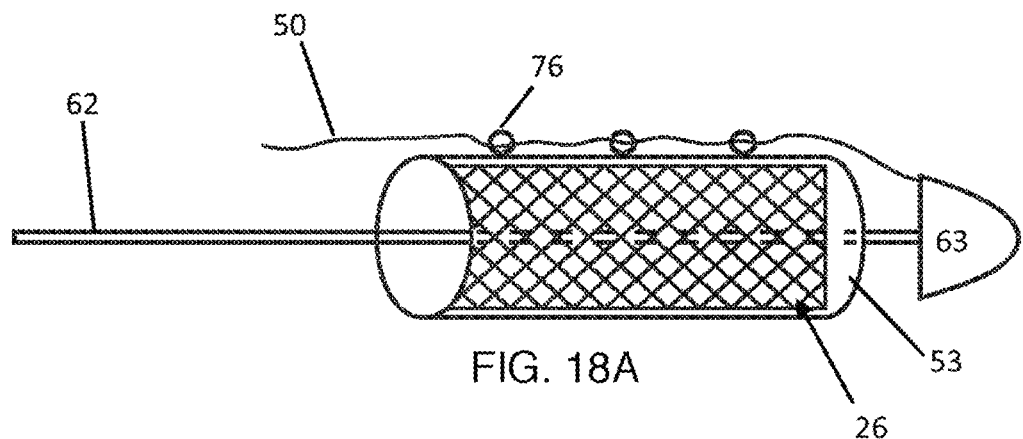
FIGS. 18A and 18B are illustrations of parallel sheaths of a deployment device constraining a stent device according to one or more embodiments of the present invention.
Figure 18B:
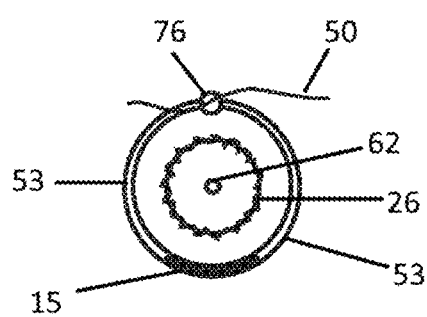
Figure 19:
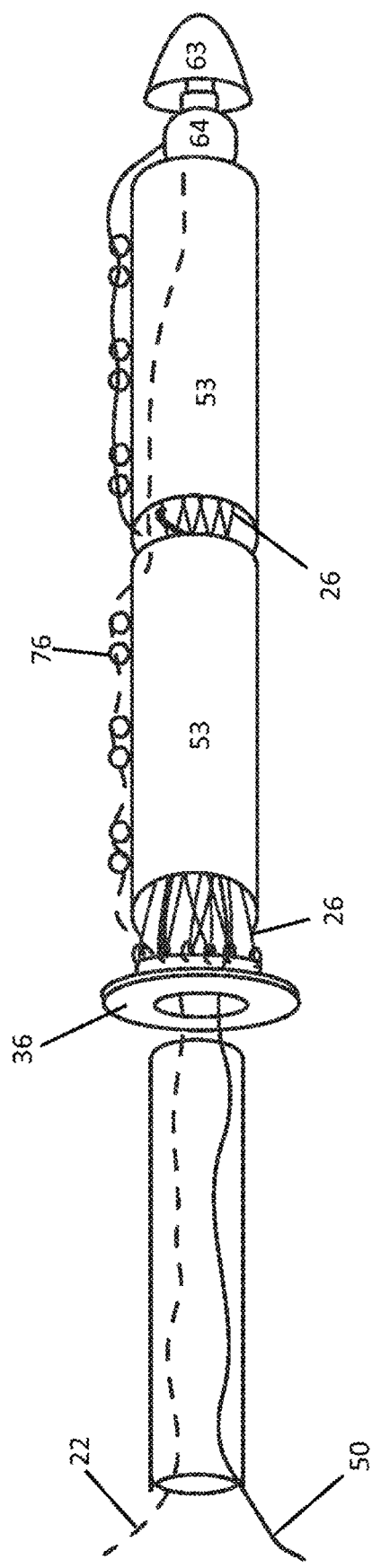
FIG. 19 is an illustration of a deployment device having sheaths constraining a stent device according to one or more embodiments of the present invention.

FIGS. 17A and 17B are illustrations of a guidewire 62 positioned within the sheaths 53 of a deployment device according to one or more embodiments of the present invention. FIGS. 18A and 18B are illustrations of a deployment device 12 having sheaths 53 and a stent device 26 positioned therewithin for deployment within an aorta 100. At least one release wire 22, 50 engages the eyelets 76 of the sheaths 53 and the tip 63 for radially constraining the stent device 26 and permitting selective expansion thereof. FIG. 19 is an illustration of the entire alternative embodiment of the deployment device 12 as described herein. Alternatively, suture material could be used to hold the two sides of the sheath 53 approximated with slipknots or passing suture technique.

In order to deploy the stent device 26 of the assembly, the chest of a patient is opened and cardiopulmonary bypass is initiated. The body is cooled down for brain and organ protection and, once adequately cold, cardiopulmonary bypass is stopped. The ascending aorta and/or aortic arch is divided and resected. The segment proximal to the innominate artery is prepared. Deployment of the stent device 26 using the deployment device 12 of the assembly 10 may be now possible once the assembly 10 has been assembled and/or prepared.

A method of deploying a stent device 26 into an aorta 100 of a patient may comprise positioning a distal portion 30 of the stent device 26 at least beyond the left subclavian artery by axially translating a distal end 20 of a rod 14 of a deployment device 12 into the aorta 100. The axial translation of the rod 14 may be provided by manipulating a handle assembly 40 of the deployment device 12. The method of deploying a stent device 26 into an aorta is illustrated in FIGS. 8A through 8H using a model aorta 100. FIG. 8A depicts the stent device 26 deployed within the aorta 100 in an initial configuration 80.

As noted supra, the stent device 26 may be engaged with the deployment device 12 in an initial configuration 80 about the rod 14. Further, the stent device 26 may include a stent portion 32 in fluid engagement with the distal portion 30 and a proximal portion 34 in fluid engagement with the stent portion 32.

In some embodiments, once the stent device 26 is deployed and/or appropriate positioning is confirmed, the method may include releasing one or more radially constraining members 24 constraining a diameter of the stent portion 32 of the stent device 26. This release may be performed by translating a first release wire 22 of the deployment device 12. Translating the release wire 22 may be performed by translating a first cap 44 engaged with the first release wire 22 and selectively engaged with a first outlet 42 of the deployment device 12, as is depicted in FIG. 8B.

In other embodiments, the method of deployment may further include releasing additional one or more radially constraining members 52 constraining the diameter of the stent portion 32. This release may be performed by translating a second release wire 50 of the deployment device 12. Translating the second release wire 50 may be performed by translating a second cap 56 engaged with the second release wire 50 and selectively engaged with the second outlet 46 of the deployment device 12.

In at least one embodiment, the one or more radially constraining members 24 radially constrain a first segment 94 of the stent portion 32 and the additional one or more radially constraining members 52 radially constrain a second segment 96 of the stent portion 32. The release wires 22, 50 may be translated in any order, and each cord 22, 50 may affect any number of segments 94, 96 or constraining members 24, 52 arranged in any number of patterns or configurations. Each release of a constraining member 24, 52 may alter the diameter of any number of segments 94, 96 of the stent portion 32 or stent device 26 to best fit the stent device 26 to the aorta 100 during and/or after deployment. This allows the stent 26 to be deployed from a proximal to distal direction, distal to proximal direction or to start the deployment in the center of the stent 26 propagating proximally or distally.

In the particular embodiment shown in FIGS. 8A through 8H the assembly 10 may be placed inside the aorta 100 and positioned with the collar 36 proximal to the origin of the innominate trunk. The collar 36 may be secured in place by stitches 74 or mechanical means. The first cap 44 may be unlocked and the release wire 22 may be pulled unraveling the first radially constraining members 24 expanding the proximal portion 34 of the stent component 26. The second release wire 50 may be now released (see FIG. 8D) and the second radially constraining members 52 are unraveled one by one under the full control of the operator while the inner rod 14 and the handle component 40 may be pulled back towards the operator. By keeping the proximal part of the assembly 10 fixated to the aorta 100, the unraveling of the second constraining members 52 one by one allows the translation of the inner rod 14 to elongate or shorten the stent component 26 as the radially constraining members 52 are unraveled thereby allowing the operator to control the functional diameter of the stent component 26 and match it to that of the aorta 100 thereby being able to treat a wide range of aortic diameters.

As depicted in FIG. 6A, a safety pin 54 may be engaged to the first cap 44 and the second cap 56. Translating the second cap 56 may be enabled when the safety pin 54 is severed or when the first cap 44 is disengaged from the first outlet 42 (see FIG. 6B).

At any point during or after deployment, the method may include modifying the length and the diameter of the stent device 26 into a deployed configuration 82 by axially translating the rod 14 within the aorta 100. For example, in FIG. 8C, the rod 14 may be translated away from the aorta 100 towards the operator, thereby expanding the deployed configuration 82 of the stent device 26 within the aorta 100. Appropriate positioning of the stent device 26 may be reconfirmed at any time. Through manipulation, modification or axial translation, the stent portion 32 may be positioned to span and engage a portion of the aortic arch to which the brachiocephalic trunk, the left common carotid artery, and the left subclavian artery attach. For example, the method may include manipulating the proximal portion 34, stent portion 32, distal portion 30, proximal graft section 90, distal graft section 92, eyelets 76 or any other component of the stent device 26 for further positioning and/or modifying the length and the diameter of the stent device 26 into a deployed configuration 82. In some embodiments, the positioning and/or modifying of the stent device 26 is limited by a stop member 64 defined about the distal end 20 of the rod 14.

Thus, as an example, by delivering the stent component 26 to the desired location in the aorta 100, the proximal portion 34 of the assembly 10 is fixated and stabilized in location. This may be done by either stitching the graft collar 36 to the transected aorta 100 or by releasing the first release wire 22 thereby expanding the proximal portion 34 of the stent component 26 allowing the stent 26 to obtain apposition against the aortic wall. Once the assembly 10 is stable in position the second release wire 50 may be pulled releasing the slip joints 52 restraining the distal portion 30 of the stent 26 while the rod 14 is translated proximally or distally like an accordion, thereby changing the length and diameter of the stent component 26 to the desired diameter and length fitting the aorta 100 and thereby pushing up and reattaching the intimal flap to the aortic wall.

Figure 8D:
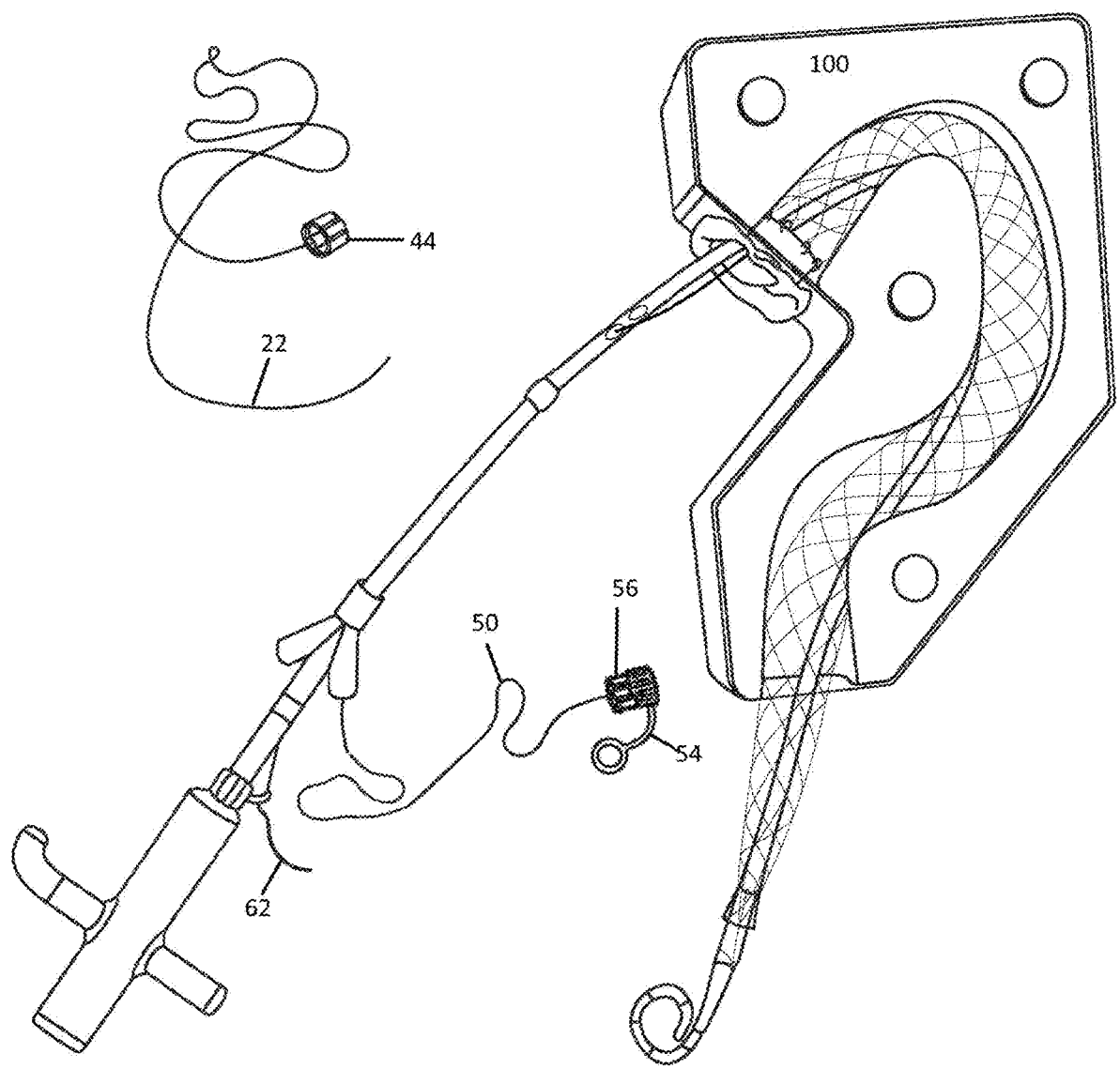
Figure 8E:
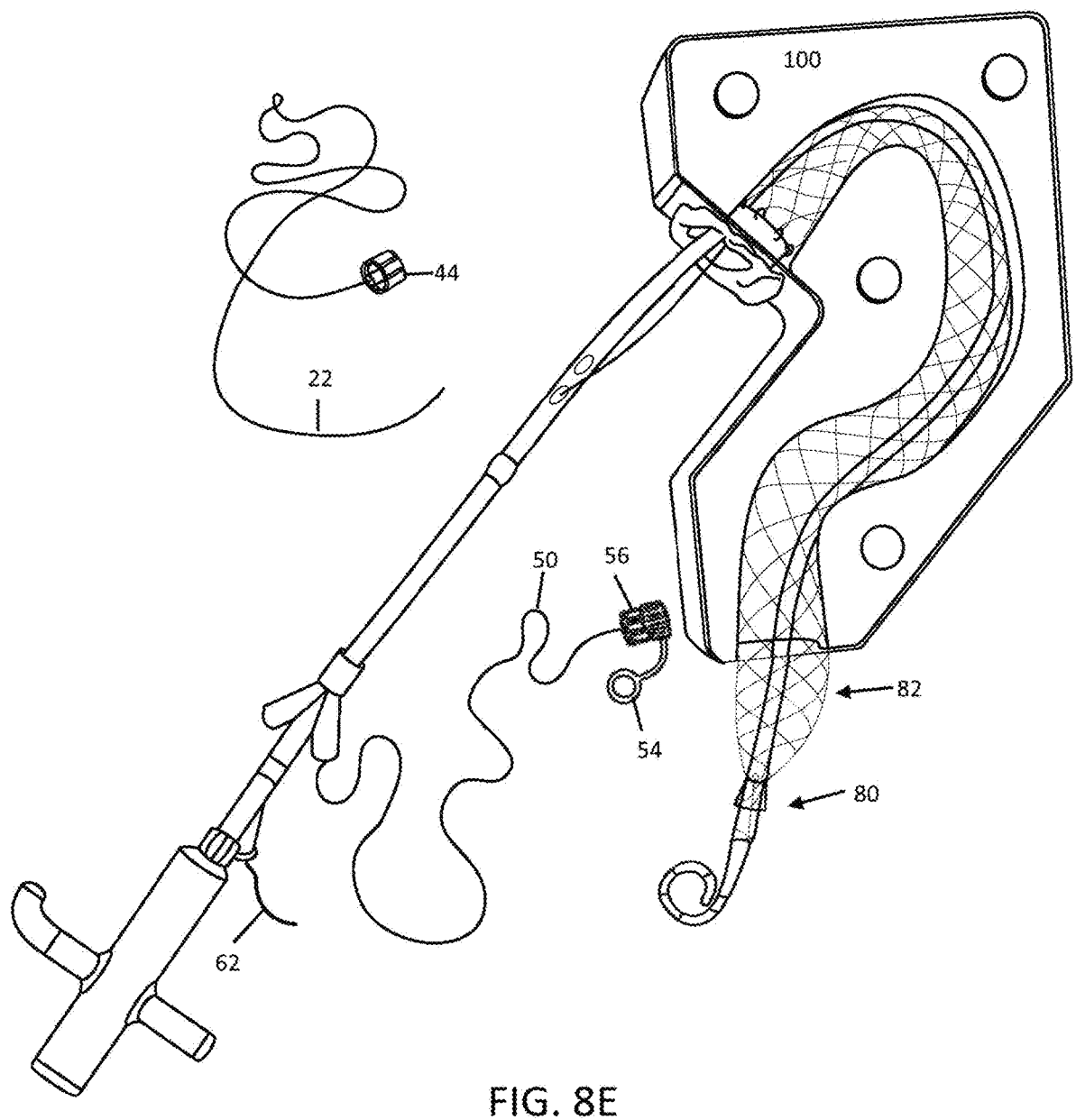
Figure 8F:
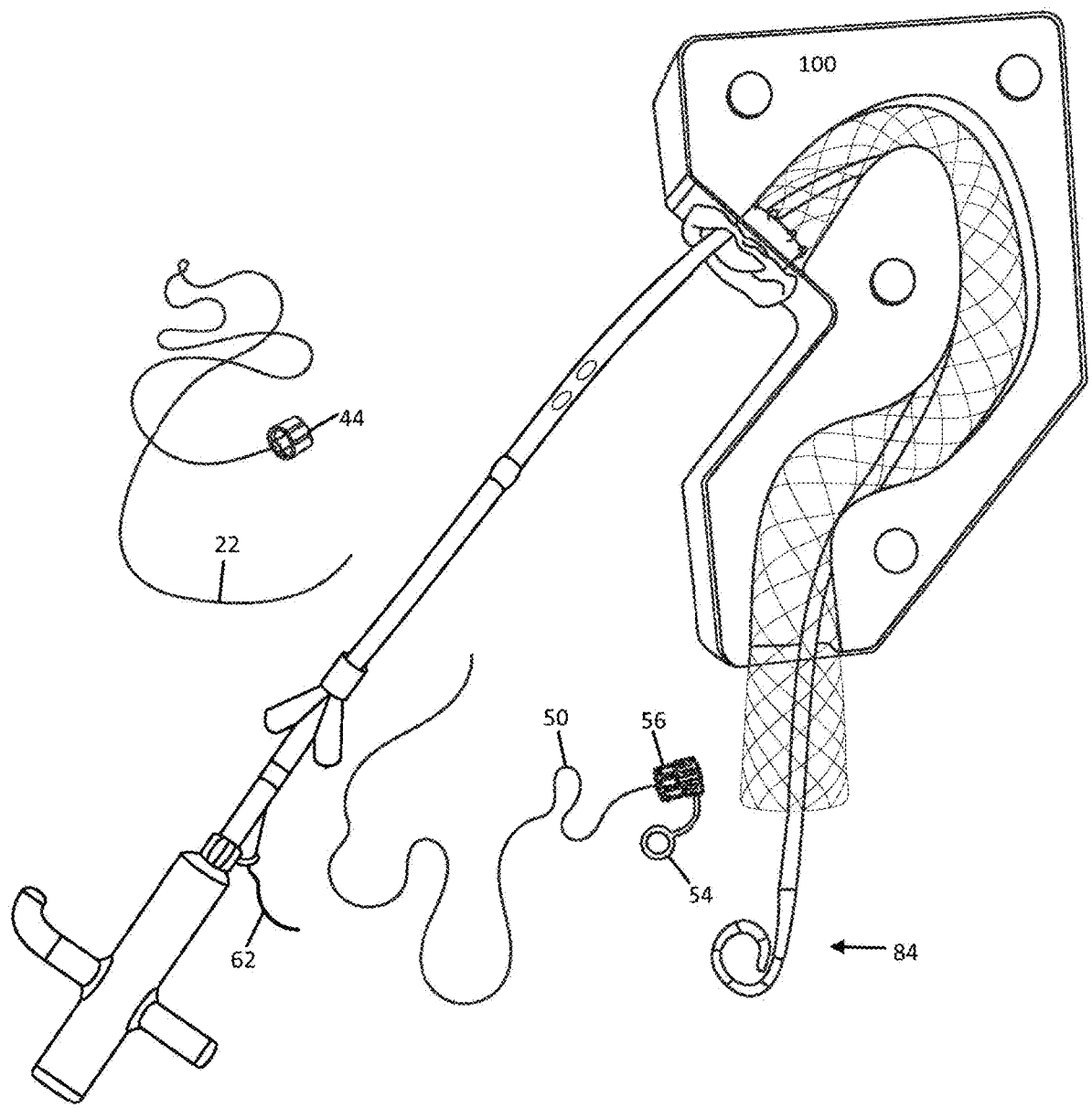
Figure 8G:
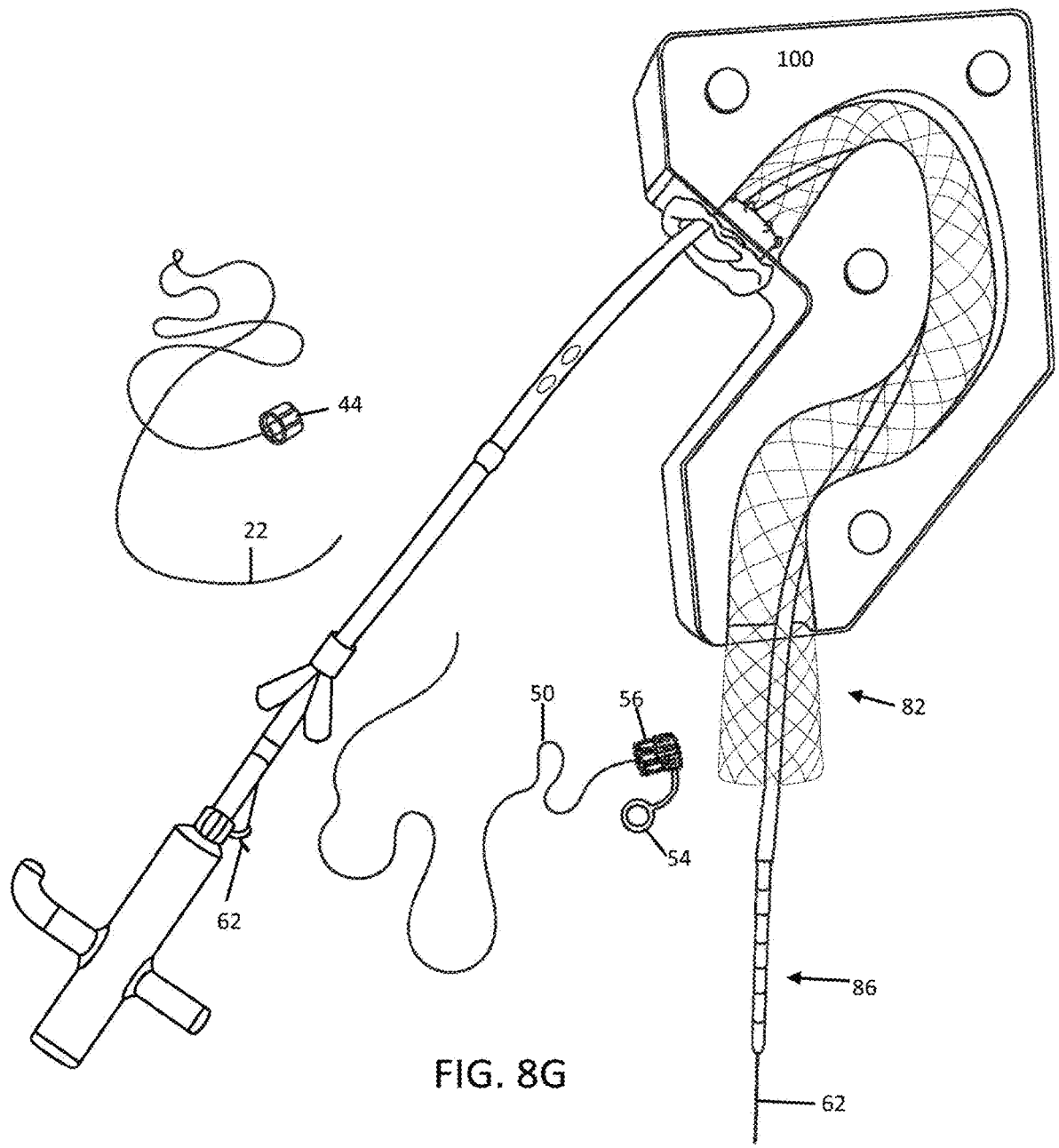
Figure 8H:
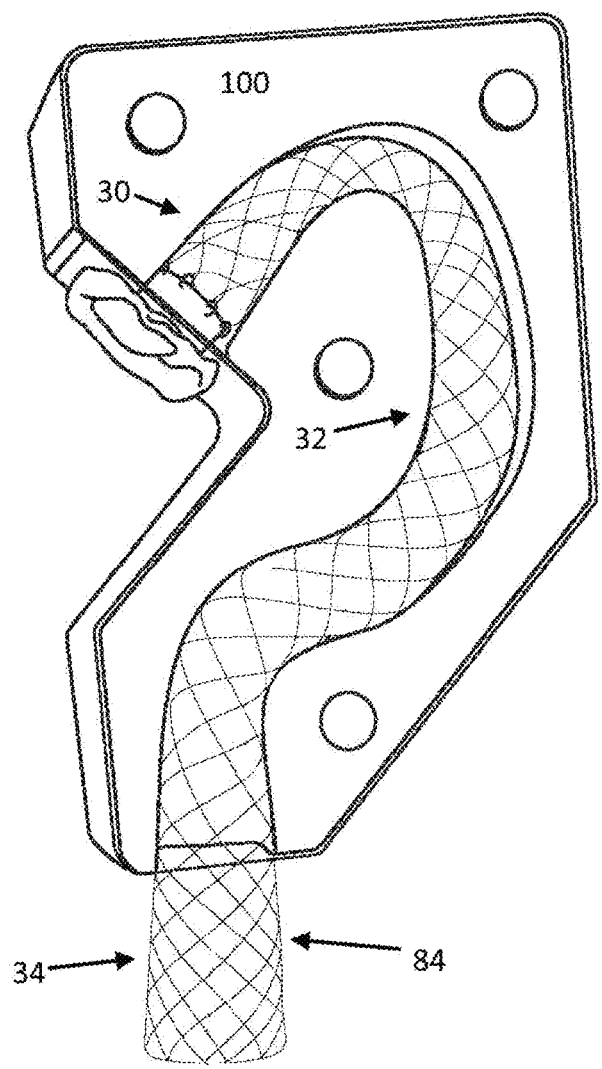

In some embodiments, once the stent device 26 has been inserted into the aorta (FIG. 8A), the first release wire 22 has been translated to expand a first segment 94 of the stent device 26 (FIG. 8B) and the rod 14 has been translated to fully deploy the first segment 94 within the aorta (FIG. 8C), the second release wire 50 may be translated to begin expansion of the second segment 96 of the stent device 26 (FIG. 8D). Before fully translating the second release wire 50, the rod 14 may again be translated to expand and position the stent device 26 within the aorta (FIG. 8E). Subsequently, the second release wire 50 may be fully translated, thereby expanding the entire second segment 96 of the stent device 26 (FIG. 8F). The guidewire 62 may then be translated to configure the tip 63 into a linear arrangement 86 for removing the rod 14 from within the stent device 26 and aorta 100 (FIG. 8G). FIG. 8H depicts a fully deployed stent device 26 within the model aorta 100.

Once the stent device 26 is deployed and/or positioned, the method may include removing the rod 14 from the aorta 100 of the patient. Removal may be performed by axially translating the rod 14 directly or by using the handle assembly 40. To ensure safe removal of the deployment device 12 from the aorta 100, a guidewire 62 may be translated to position the tip 63 into a linear arrangement 86. The method may further include advancing a guidewire 62 extending through a third outlet 60 of the deployment device 12 through a tip 63 defined by the distal end 20 of the rod 14, causing the tip 63 to change from a non-linear arrangement 84 to a linear arrangement 86. In some embodiments, the tip 73 may be pushed distally to fully disengage the stent device 26 for removal of the deployment device 12 from the aorta 100.

For embodiments of the assembly 10 including a collar 36 engaged to the proximal portion 34, the method may include attaching the collar 36 to the aorta 100 or another stent. For embodiments of the assembly 10 including a distal portion 30 of the stent device 26, the method may include attaching the distal portion 30 to the aorta 100, a distal graft section 92 or another stent. The attachment of the proximal portion 34 or the distal portion 30 may be performed prior to radial expansion of the stent device 26, prior to final deployment of the stent device 26, or after final deployment of the stent device 26.

As disclosed herein, the stent device 26 may be deployed independent from graft sections 90, 92, i.e. the operator will open the aorta 100 as described supra and deploy the stent device 26 into the aortic arch and the descending aorta to reattach the dissection flap. Once the stent device 26 is delivered to its intended location, a polyester proximal graft section 92 may be used as a unique separate entity, the distal end of which is anastomosed to the aortic arch at or near the junction of the attachment of the stent. The proximal end of the proximal graft section 92 may be anastomosed to the sinutubular junction or a valved conduit. This effectively replaces the ascending aorta. As yet another embodiment, the stent device 26 may be implanted over a deployment device 12 where the stent device 26 is unsheathed during deployment. This may entail removing a protective sheath(s) 53 to uncover the stent 26 and allow it to expand. Alternatively a conventional sheathed delivery device may be used. The proximal, stent and/or the distal portions 30, 32, 34 of the stent device 26 may be captured by a release mechanism(s) 24, 52, 64, 63 that control accurate and sequential release of the stent.

To control the release of the stent device 26 and reduce the profile of the stent device 26 on the deployment device 12, the stent device 26 may be mounted and stretched over the rod 14 and stabilized and bound using release wires 22, 50, which may be comprised of Tevdek (or other) suture material, effectively creating multiple restraining points. In other embodiments, one or more longitudinal release wires 22, 50 may be used and slipknots are created to hold the stent device 26 onto the rod 14. The slipknots may jump to the next holding position at regular intervals. Depending on the start and the direction of positioning of the slipknots, the stent device 26 may be deployed in multiple combinations of directions, i.e. proximal to distal, distal to proximal or from the middle of the hybrid graft. If two or more release wire 22, 50 systems with independent slipknots are used, then different parts of the stent device 26 may be unwrapped and expanded independent of each other and in different directions.

A terminal end of the release wires 22, 50 may be attached to a cap 44, 56 that screws or otherwise selectively engages into outlets 42, 46 for safety. Once the operator is satisfied with the positioning of the stent device 26, the cap(s) 44, 56 may be unscrewed, released, and translated. The attached release wire(s) 22, 50 may be pulled to release and expand the braided portion of the stent device 26.

The combination of the stent device 26 and the deployment device 12 including the described slipknots allows very unique properties that include that the operator is in full control of the length and diameter of the stent device 26. Conventional grafts and stent grafts by virtue of their graft material are fixed in length and diameter. In contrast, the stent device described herein can be elongated or shortened thereby decreasing or increasing its diameter. Thus by sequential stepwise unwrapping of the radially constraining members 24, 52, one end of the stent device will be allowed to expand first reaching the maximum diameter of the aorta 100 and become fixed in place. At this stage the operator is able to manipulate and position various portions of the stent device 26 and/or deployment device 12 proximally or distally by axially translating the deployment device 12 while in a controlled fashion pulling on the release wire and unraveling the constraining member 24, 52, actively adjusting the diameter and length of the stent device 26 to that suitable for the particular aortic dimension that is being treated. The obvious advantages of this technology is the in-vivo fitting of the stent device 26 to the aortic anatomy, and only one or two sizes of the stent device may be needed to accommodate the majority of aortic dimensions in patients.

As illustrated in FIGS. 4A and 4B, the tip 63 capable of both a non-linear arrangement 84 and linear arrangement 86 permits the atraumatic introduction of the stent device 26 into the aorta 100. Once the stent device 26 is deployed, the curled tip 63 may be straightened into a linear arrangement 86 as the deployment system is being retracted from the aorta 100, thereby avoiding entanglement with the stent device 26 or aorta 100. The tip 63 may be hollow with a guidewire 62 that is continuous and passing through the center of the deployment device 12. Passage of the guidewire 62 may also reconfigures the tip 63 from the initially non-linear arrangement 84 to the linear arrangement 86 for smooth delivery of the stent device 26. The guidewire 62 may terminate just distal to the handle assembly 40 where the guidewire 62 can enter or exit the deployment device 12 through a third outlet 60. In addition the tip 63 can be used to inject contrast into the aorta 100 using the guidewire 62. This enables the operator to perform angiograms while deploying the stent device 26 rather than using a separate angiographic catheter.

In some embodiments, the stent device 26 may have a diameter in an initial configuration 80 of 40 mm when the length of the stent device 26 is 85 mm. In such an embodiment, the stent device 26 may stretch to 200 mm, therefore reducing the diameter to 20 mm. Such properties are useful for treatment of various aortas 100 with different diameters. By using the assembly 10 described in this document, the operator will have the ability to fully control the length and diameter of the stent device 26 to match the anatomies of most patients' aorta 100. This offers a tremendous flexibility for patient treatment and only one or two sizes of stent devices 26 may be required to match the anatomy of the patient population. In addition, deploying the stent device 26 on one end allows fixation of one end of the stent device 26. Once one end of the stent device 26 is fixed the memory shape wire of the stent 26 and the inertia in the stent 26 will pull back the remainder of the stent 26 and shorten it thereby increasing the diameter of the stent 26. The expansion of the stent 26 will only stop once the outer surface of the stent contacts the aortic wall and is therefore inhibited from further expansion. This "auto-sizing" and expansion feature is responsible for lifting and tacking the intimal flap of the dissection and fuse it back to the wall of the aorta 100. Similarly the stent 26 expansion may be mechanically assisted by pulling back on the rod 14 of the deployment device 12 prior to fully releasing the stent device 26. This system also allows the operator to lengthen and reduce the diameter of the stent 26 by translating the rod 14 in the opposite direction along the central axis of the stent 26 and the aorta 100.

It will be appreciated that the devices and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this disclosure have been explained and illustrated in exemplary embodiments.

It is intended that the scope of the present methods and apparatuses be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

The scope of the disclosure should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the disclosure and that the method and apparatus within the scope of these claims and their equivalents be covered thereby. In sum, it should be understood that the disclosure is capable of modification and variation and is limited only by the following claims.

The invention claimed is:

1. An assembly comprising:
 a deployment device comprising:
  a rod translatable within an aorta of a patient and having an operator end and a distal end;
  one or more radially constraining members;
  a first release wire configured for releasing the one or more radially constraining members, and
 a stent device comprising:
  a distal portion for being engageably received in the aortic arch of the patient and extending beyond the left subclavian artery when implanted;
  a stent portion fluidly engaged with the distal portion, wherein the stent portion comprises an uncovered, braided stent member,
  wherein the stent portion is configured to span a portion of the aortic arch to which the brachiocephalic trunk, left common carotid artery, and left subclavian artery attach when implanted in the aortic arch such that blood flows through the uncovered, braided stent member into the brachiocephalic trunk, left common carotid artery, and left subclavian artery;
  a proximal portion fluidly engaged with the stent portion,
  wherein the stent device is configured to be engaged with the deployment device so as to be deployed within the aorta of the patient in a deployed configuration while allowing a diameter and a length of the stent device to be varied to conform to that of the patient's aortic anatomy;
  wherein the stent device includes a collar engaged with the proximal portion, the collar configured for being selectively engaged with the aorta and being formed of a graft material,
 wherein the stent device is engaged with the deployment device in an initial configuration, wherein the one or more radially constraining members are configured to constrain a diameter of the stent device, and
 wherein the diameter and the length of the stent device in the deployed configuration can be altered by axial translation of the rod and releasing the one or more of the radially constraining members by translation of the first release wire, wherein the one or more radially constraining members comprise at least one slip joint and wrap around the stent portion at spaced-apart portions along a length of the stent portion extending from about a proximal end to about a distal end of the stent portion.

2. The assembly according to claim 1, wherein the deployment device includes a handle assembly for providing axial translation of the rod and defines a first outlet from which the first release wire extends, wherein the first release wire is configured for releasing the one or more radially constraining members, and includes a first cap selectively receivable by the first outlet, wherein the first release wire is engaged with the first cap.

3. The assembly according to claim 2, wherein the deployment device defines a second outlet from which a second release wire extends, wherein the second release wire is configured for releasing additional one or more radially constraining members.

4. The assembly according to claim 3, wherein the one or more radially constraining members are configured to release a first segment of the stent device, and the additional one or more radially constraining members are configured to release a second segment of the stent device.

5. The assembly according to claim 3, wherein the deployment device defines a third outlet through which a guidewire extends, wherein the rod defines a tip on the distal end that has an initially non-linear arrangement, and wherein advancement of the guidewire through the tip causes the tip to define a linear arrangement.

6. The assembly according to claim 5, further defining a stop member on the distal end of the rod for prohibiting movement of the stent device therebeyond.

7. The assembly according to claim 1, wherein the stent portion is a braided stent member and/or an uncovered, gridded pattern.

8. The assembly according to claim 1, wherein the stent device includes a biodegradable scaffold for engaging an anatomical feature of a patient.

9. The assembly according to claim 1, further comprising:
 a proximal graft section engaged to the proximal portion of the stent device;
 a distal graft section engaged to the distal portion of the stent device; or
 both the proximal graft section and the distal graft section, wherein the proximal graft section, the distal graft section, or both are supported internally or externally by a metallic frame.

10. The assembly according to claim 1, wherein the one or more radially constraining members include at least one slip joint.

* * * * *